United States Patent [19]

Li et al.

[11] Patent Number: 6,143,519
[45] Date of Patent: Nov. 7, 2000

[54] HUMAN ENDOTHELIN-BOMBESIN RECEPTOR

[75] Inventors: Yi Li, Sunnyvale, Calif.; Craig A. Rosen, Laytonsville, Md.; Chandrika Kumar, West Windsor, N.J.

[73] Assignee: Human Genome Sciences, Inc., Rockville, Md.

[21] Appl. No.: 09/030,970

[22] Filed: Feb. 26, 1998

Related U.S. Application Data

[60] Division of application No. 08/465,687, Jun. 6, 1995, Pat. No. 5,750,370, which is a continuation-in-part of application No. PCT/US94/11843, Oct. 17, 1994.

[51] Int. Cl.⁷ .................................................. C12N 15/00
[52] U.S. Cl. .......................... 435/69.1; 530/350; 530/300; 435/325; 435/320.1; 435/252.3; 435/254.11; 536/23.5; 536/23.1
[58] Field of Search ................................. 435/69.1, 325, 435/320.1, 300, 252.3, 254.11; 530/350; 536/23.5, 23.1

[56] References Cited

FOREIGN PATENT DOCUMENTS 522 868  1/1993  European Pat. Off. .

OTHER PUBLICATIONS

Corjay, et al. "Two Distinct Bombesin Receptor Subtypes Are Expressed and Functional in Human Lung Carcinoma Cells," *The Journal of Biological Chemistry*, vol. 266, No. 28, pp.18771–18779 (1991).
Hosoda, et al. "Targeted and Natural (Piebald–Lethal) Mutations of Endothelin–B Receptor Gene Produce Megacolon Associated with Spotted Coat Color in Mice," *Cell*, vol. 79, pp. 1267–1276 (1994).
Hori, et al. "Distinct Tissue Distribution and Celluaral Localization of Two Messenger Ribonucleic Acids Encoding Different Subtypes of Rat Endothelin Receptors," *Endocrinology*, vol. 130, No. 4, pp. 1885–1895 (1992).
Geneseq Accession No. Q39831 (May–20–1993).
Geneseq Accession No. Q59243 (Mar.–16–1994).
Genbank Accession No. M62108 (May–26–1992).
Adachi et al. (1991) Biochem. & Biophys. Res. Comm. 180(3):1267–1270.
Arai et al. (1990) Nature 348:730–732.
Elshourbagy et al. (1991) Mol. Pharma. 41:465–473.
Hayzer et al. (1992) Amer. J. Med. Sci. 304(4):233–238.
Hosoda et al. (1991) FEBS 287(12):23–26.
Miller et al. (1993) TIPS 14:54–60.
Sakurai et al. (1990) Nature 348:732–735.
Zachary et al. (1987) J. Biol. Chem. 262(9):3947–3950.
Adams et al., Expressed Sequence Tag human gene marker EST00359, Geneseq Accession Number Q39845, Jan. 1993.

*Primary Examiner*—Anthony Caputa
*Assistant Examiner*—Eliane Lazar-Wesley
*Attorney, Agent, or Firm*—Human Genome Sciences,Inc.

[57] ABSTRACT

A human endothelin-bombesin receptor polypeptide and DNA (RNA) encoding such polypeptide and a procedure for producing such polypeptide by recombinant techniques is disclosed. Also disclosed are methods for utilizing such polypeptide for identifying agonists and antagonists to such polypeptide. Agonists to the endothelin-bombesin receptor polypeptide of the present invention may be used to treat asthma, Parkinson's Disease, acute heart failure, hypotension and osteoporosis. Antagonists against such polypeptides may be used therapeutically to treat hypertension, ulcerigenesis, subarachnoid hemorrhage, asthma, tumors, ciclosporin toxicity, cancer and septic shock. Also disclosed are diagnostic methods for detecting mutations in the polynucleotides of the present invention and for detecting levels of the soluble polypeptides in samples derived from a host.

48 Claims, 21 Drawing Sheets

FIG. 1A

```
         10         30         50
CCCACTATGTTGGCCAGGATGGTCTTGATTTCTTGACCTCGTGTTCTGCCCGCCCTCTACC
         70         90        110
TCCCAAAGTGCCGGGATTACAGGCGTGACTGCTGTGCCCGGCCCCAGCATCACTTTTATA
        130        150        170
GCTTTCTGTGCCTCTCCTCTGGGCCTTGGTGTATGAAGCCACTTGCCTTTCTCTGTTGG
        190        210        230
GAAGCGAGCAGAATCAGATTGCTACTCATGATGCAGTCCGGGCAGGGCATACTGTCACCT
        250        270        290
TTGGCTGTGGACACAGTGTCAGGATAGGGGAGAAGCCCTTTAGGTCCGTCTTCTTGACA
        310        330        350
CAGCCCCTCCTACCCTGGTTACGCTGGTGTTCGCTGGTGTTAGACAACCAAGACACTTGA
        370        390        410
GAATTATGCTGTCCTCAGAATGTCTGATGAAAGAACAGATTCACTTTTTGGACACAATG
        430        450        470
CCCATTAGCCATCTTTGGCAGTGTTCTGATCAAAGTTCCCCATGCCTGCTCTAGGAAA
        490        510        530
GTAAACTTTTTCAGAATAAATCCTCAAATGGATTACTGAGTAGTCTCTTGCACCATTCCC
        550        570        590
ATCAGCCTAATCAGACTGAATGGTCACGCTCAGTGCAAAAGCTGTTTTGCTGTGTTAGGAT
```

FIG. 1B

```
                                                                      .
             610           630           650
              .             .             .
GTTTCAGTGTGTTTCTTGTCTTTCCTGGAACAGTTCAGTGTTAAATTTAGTAATTCAATC
              670           690           710
              .             .             .
CTGACCAGTGTAAACCCACTTAATTATTGCAGCCTAAAGAATTCAGCTACTTCTACTCTT
              730           750           770
              .             .             .
CATAAATGTGCCCAAGTAAATATGTGTTTTAATATTCAACCCTGAAAATTAGTAATTC
              790           810           830
              .             .             .
AGATGATAAAAGCTCATGTGTTTGGTGTCTTTGTACTCAGATTGTGAACAGGCATATTCA
              850           870           890
              .             .             .
CTGATTTAGACTTAGTATACTTGATGAGAATGCTCAGGTTGAAGAGATAGTTCTGTCAGC
              910           930           950
              .             .             .
AATCCAACATCTATAGCAATGTGGAAAAAGTAATCAACTCATATTTCACGAATTGATGT
              970           990           1010
              .             .             .
ATGTTGTGATTTAGAGGGCATGAGATAAAGTTTATATTTGAACTGTGTGGGGTAGGGGGA
              1030          1050          1070
              .             .             .
AGAAGAGGTTGCTTAAGCAAATGGGGGGTGATTGAGGAACAAGATGTCTCTAAGATGAG
              1090          1110          1130
              .             .             .
AAGTTATTTCTTGCATCATAGAAGCACTCTCTCCACCCGGGAGTGATTGTTAACTAT
              1150          1170          1190
              .             .             .
AAATCATTTATATCTGTACATTAAAGCAGATTCCCTCAATTAGGCAAATTTGGTTAGCCA
```

FIG. 1C

```
         1210                 1230                  1250
AGCCCAAGTTATTGTTTGTACTTGAAAGTAATAAAGCTGCATTTCCTTAAAAATATATTC
              1270                 1290                  1310
TGTAGTTAAGACTTTGTCTTGCTTCCGGAATTCCGTGTTTTTCTTTCCTCTAGAGACCT
              1330                 1350                  1370
CGGCTTGCAACTGGATCAAACGCTGTCGAAAGGATGTAAATAGGCAGAGCAACTGTACC
              1390                 1410                  1430
AAGAAGGCCACCACCCCCACCCCAAAGGCAGTGAGGAGTGTGGGGCTTCGTCTGGGCTCCC
              1450                 1470                  1490
CCGAGTCTCAACAGTAATCAACAGTCAGGTGTTGATTGCAACTTTTCAAGGTCAGCCACC
              1510                 1530                  1550
GGGAGTAGCCTATTCCCTCTAGGAACCTTGGAGGGCATACCTTGCTGGGACTCAACTTGG
              1570                 1590                  1610
CTGAGAAATGCACAAGATGCCAAAGGAGGAAGGATTATAGGGGCGTGTGTGTGACCCCC
              1630                 1650                  1670
AAGACCGATCTTCCGCTATCACCCTAATCTCCGGTTCCCCGCTACCCGGCGGGGGTGAG
              1690                 1710                  1730
TATGTGACATGTGCCTAACTCTCAGCAGCAACTTCGGCAGCAGGTGTCGATCCTAACTAA
              1750                 1770                  1790
GCAGGAGCTGCGGCTGCGGGTGTGCCCTCACCCAAGCCATGCGAGCCCCGGGCGCGCTTC
```

FIG. 1D

```
                                    M   R   A   P   G   A   L   L
                                                    1850
TCGCCCGCATGTCGCGGCTACTGCTCTCTGCTCAAGGTGTCTGCCTCTTCTGCCC
 A  R  M  S  R  L  L  L  L  L  K  V  S  A  S  S  A  L
1810        1830        1870        1890                1910

TCGGGGTCGCCCCCTGCTGGTCCAGAAACGAAACTGTCTGGGGAGAGCTGTCACCTACAG
 G  V  A  P  A  S  R  N  E  T  C  L  G  E  S  C  A  P  T  V
        1930                1950                1970

TGATCCAGCGCCGCGGGACGCCTGGGACCGGGGAAATTCTCAAGAGACGTTCTGC
 I  Q  R  R  G  R  D  A  W  G  P  G  N  S  A  R  D  V  L  R
        1990                2010                2030

GAGCCCGAGCACCCAGGAGGAGCAGGGGCAGCGTTCTTGCGGGACCCTCCTGGGACC
 A  R  P  R  E  E  Q  G  A  A  F  L  A  G  P  S  W  D  L
        2050                2070                2090

TGCCGGCGGCCCCGGACCCCGGCTGCAGGCAGAGAGGGCGAGGCGTCGACAGCCG
 P  A  A  P  D  R  D  P  A  A  G  R  G  A  E  A  S  T  A  G
        2110                2130                2150

GACCCCCGGGACCTCCAACCAGGCCACCTGTCCCCTGAGGTGGAAAGGTGCTCGGGGTC
 P  P  G  P  P  T  R  P  P  V  P  W  R  W  K  G  A  R  G  Q
        2170                2190                2210

AGGAGCCTTCTGAAACTTTGGGGAGAGGAACCCACGGCCCTCCAGCTCTTCCTTCAGA
 E  P  S  E  T  L  G  R  G  N  P  T  A  L  Q  L  F  L  Q  I
        2230                2250                2270
```

FIG. 1E

```
TCTCAGAGGAGGAAGAGAAGGGTCCCAGAGGCGCTGTCATTTCCGGGCGTAGCCAGGAGC
 S  E  E  E  E  K  G  P  R  G  A  V  I  S  G  R  S  Q  E  Q
                         2290                    2310
AGAGTGTGAAGACAGTCCCCGGAGCCAGCGATCTTTTTACTGTCCAAGGAGAGCCGGGA
 S  V  K  T  V  P  G  A  S  D  L  F  Y  C  P  R  R  A  G  K
           2350                    2370                  2390
AACTCCAGGGTTCCCACCACAAGCCCCTGTCCAAGACGGCCAATGGACTGGCGGGCACG
 L  Q  G  S  H  H  K  P  L  S  K  T  A  N  G  L  A  G  H  E
           2410                    2430                  2450
AAGGGTGGACAATTGCACTCCCCGGGCGCCGGCCCAGAATGGATCCTTGGGTGAAG
 G  W  T  I  A  L  P  G  R  A  L  A  Q  N  G  S  L  G  E  G
           2470                    2490                  2510
GAATCCATGATCCTTGGGGGTCCCCGCCGGGGAAACAGCACGAACCGCGTGTGAGACTGA
 I  H  D  P  G  G  P  R  R  G  N  S  T  N  R  R  V  R  L  K
           2530                    2550                  2570
AGAACCCCTTCTACCCGCTGACCCAGGAGTCCTATGGAGCCTACGCGGTCATGTGTCTGT
 N  P  F  Y  P  L  T  Q  E  S  Y  G  A  Y  A  V  M  C  L  S
           2590                    2610                  2630
CCGTGGTGATCTTCGGGACCGGCATCATTGGCAACCTGGCGGTGATGTGCATCGTGTGCC
 V  V  I  F  G  T  G  I  I  G  N  L  A  V  M  C  I  V  C  H
           2650                    2670                  2690
ACAACTACTACATGCGGAGCATCTCCAACTCCCCTCTTGGCCAACCTGGTCTCTTCTGGGACT
```

FIG. 1F

```
  N  Y  Y  M  R  S  I  S  N  S  L  L  A  N  L  V  F  W  D  F
     2710                  2730                  2750
TTCTCATCATCTTCTTCTGCCTTCCGCTGGTCATCTTCCACGAGCTGACCAAGAAGTGGC
  L  I  F  F  C  L  P  L  V  I  F  H  E  L  T  K  K  W  L
     2770                  2790                  2810
TGGTGGAGGACTTCTCCTGCAAGATCGTGCCCTATATAGAGGTCGCTTCTCTGGAGTCA
  V  E  D  F  S  C  K  I  V  P  Y  I  E  V  A  S  L  G  V  T
     2830                  2850                  2870
CCACTTTCACCTTATGTGCTCTGTGCATAGACCGCTTCCGTGCCGCCACCAACGTACAGA
  T  F  T  L  C  A  L  C  I  D  R  F  R  A  A  T  N  V  Q  M
     2890                  2910                  2930
TGTACTACGAAATGATCGAAAACTGTTCCTCAACTGCCAAACTGGCTGTTATATGGG
  Y  Y  E  M  I  E  N  C  S  S  T  T  A  K  L  A  V  I  W  V
     2950                  2970                  2990
TGGGAGCTCTATTGTTAGCACTTCCAGAAGTTGTCCTCCGCCAGCTGAGCAAGGAGGATT
  G  A  L  L  L  A  L  P  E  V  V  L  R  Q  L  S  K  E  D  L
     3010                  3030                  3050
TGGGGTTAGTGGCCGAGCTCCGGCAGAAAGGTCATTATTAAGATCTCTCCTGATTTAC
  G  F  S  G  R  A  P  A  E  R  C  I  I  K  I  S  P  D  L  P
     3070                  3090                  3110
CAGACACCATCTATGTTCTAGCCCTACGACAGTGCGAGACTGTGGTGGTATTTG
  D  T  I  Y  V  L  A  L  T  Y  D  S  A  R  L  W  W  Y  F  G
     3130                  3150                  3170
```

FIG. 1G

```
GCTGTACTTTGTTGCCACGCTTTCACCATCACCTGCTCTTCTAGTGACTGCGAGGA
 C  Y  F  C  L  P  T  L  F  T  I  T  C  S  L  V  T  A  R  K
                    3190                      3210                      3230

AAATCCGCAAAGCAGAGAAAGCCTGTACCCGAGGGAATAAACGGCAGATTCAACTAGAGA
 I  R  K  A  E  K  A  C  T  R  G  N  K  R  Q  I  Q  L  E  S
                    3250                      3270                      3290

GTCAGATGAACTGTACAGTGGCACTGACCATTTTATATGGATTGGGCATTATTCCTG
 Q  M  N  C  T  V  V  A  L  T  I  L  Y  G  L  G  I  I  P  E
                    3310                      3330                      3350

AAAATATCTGCAACATTGTACTGCCTACATGGCTACAGGGGTTTCACAGCAGACAATGG
 N  I  C  N  I  V  T  A  Y  M  A  T  G  V  S  Q  Q  T  M  D
                    3370                      3390                      3410

ACCTCCTTAATATCATCAGCCAGTTCCTTTGTTCTTTAAGTCCCTGTGTCACCCCAGTCC
 L  L  N  I  I  S  Q  F  L  L  F  F  K  S  C  V  T  P  V  L
                    3430                      3450                      3470

TCCTTTTCTGTCTCTGCAAACCCTTCAGTCGGGCCTTCATGGAGTGCTGCTGTGTTGCT
 L  F  C  L  C  K  P  F  S  R  A  F  M  E  C  C  C  C  C  C
                    3490                      3510                      3530

GTGAGGAATGCATTCAGAGTCTTCAACGGTGACCAGTGATGACAATGACAACGAGTACA
 E  E  C  I  Q  K  S  S  T  V  T  S  D  D  N  D  N  E  Y  T
                    3550                      3570                      3590

CCACGGAACTCTCGCCTTTCAGTGCCATACGCCGTGAAATGTCCACTTTTGCTT
```

FIG. 1H

```
T  E  L  E  L  S  P  F  S  A  I  R  R  E  M  S  T  F  A  S
CTGTCGGAACTCATTGCTGAAGGACAGTACTGGTTGGGTCAGATTTATTGTTTGATTT
3610                      3630                      3650
V  G  T  H  C  *
TCATATCCCGTGAAAGTTTTAATTCATATTTTCCTTATAGGGAAAAAATGCAAAAAGA
3670                      3690                      3710                      3730                      3750                      3770
AACAATAAAGAAAGAAATATTAACTACTGTAGAACTGATTTACAAATAATATTTGTGC
3790                      3810                      3830
TTTGAAAAAAGTTTCTATTTAGTTATTTAAGAAGAATGAGAAGGCCAATAGTTTTAGAT
3850                      3870                      3890
TATTTTATCTGGTATGGTGCTAATATTTTATTTGAAAAATACAATTATTGTATATTAATTATAGCAATG
3910                      3930                      3950                      3970                      3990                      4010
AATTGCTAACGTTTTTTCTTCTTTAAAAATACAATTATTGAGTTGTGATTGAAAGTATGTTGTATATGGTATTG
4030                      4050                      4070
TGAGATGATTGTACTGGAAGCATTCACAAAGTAGCACCAAATAAATTACACTTTATTC
4090                      4110                      4130
TTTAATGTCATTGTCAATCTACTTTTAACCAATATTCAATAAATCTTCTAATGCCTTAA
4150
AAAAAAAAAAAAAA
```

```
- - - - - A C - - S - - -   Majority
        40          50
C L G E S C A P T V I Q     49.pep.4/29
- - - - - G C V I S D - -   HumanETA.PEP
- - - - - A C G L S R I W   HuETBR.PEP
- - - - - A C L M V G V C   FROG.ET3R.PEP
- - - - - - - - - - - - -   GRP-R
- - - - - - - - - - - - -   NeuroMBR/rat

- X X X S - D - - - - -     Majority
      90          100
P A A P D R D P A A G R     49.pep.4/29
- - - - - - S - - - - -     HumanETA.PEP
W P K G S N A - - - - -     HuETBR.PEP
V Q L D S - - - - - - -     FROG.ET3R.PEP
- H S A D - - - - - - -     GRP-R
- E V W E N D - - - - -     NeuroMBR/rat

- - - - - - F L P X S D     Majority
       140         150
P T A L Q L F L Q I S E     49.pep.4/29
- - - - - - F L V T T H     HumanETA.PEP
- - - - - - S L A R S L     HuETBR.PEP
- - - - - - - - I Q N N     FROG.ET3R.PEP
- - - - - - - L P V N D     GRP-R
- - - - - - F L P D S D     NeuroMBR/rat

- - - - - - - - - - - -     Majority
      190         200
L Q G S H H K P L S K T     49.pep.4/29
- - - - - - - - - - - -     HumanETA.PEP
- - - - - - - - - - - -     HuETBR.PEP
- - - - - - - - - - - -     FROG.ET3R.PEP
- - - - - - - - - - - -     GRP-R
- - - - - - - - - - - -     NeuroMBR/rat
```

```
- - - - - - - - K I K X A    Majority
        240           250
N S T N R R V R L K N P      49.pep.4/29
- - - - - - - T K I T S A    HumanETA.PEP
- - - - - - - I E I K E T    HuETBR.PEP
- - - - - - - A K I R H A    FROG.ET3R.PEP
- - - - - - - - - - P G I    GRP-R
- - - - - - - - - - E L V    NeuroMBR/rat N K Y M R N G P N I L I      Majority
        290           300
N Y Y M R S I S N S L L      49.pep.4/29
N K Y M R N G P N A L I      HumanETA.PEP
N K C M R N G P N I L I      HuETBR.PEP
N K C M R N G P N V L I      FROG.ET3R.PEP
V K S M R N V P N L F I      GRP-R
N S T M R S V P N I F I      NeuroMBR/rat G C K L V P F I Q L A S      Majority
        340           350
- C K I V P Y I E V A S      49.pep.4/29
L C K L F P F L Q K S S      HumanETA.PEP
M C K L V P F I Q K A S      HuETBR.PEP
- - - I Y Q L V H L Y R      FROG.ET3R.PEP
G C K L I P F I Q L T S      GRP-R
G C K L I P A I Q L T S      NeuroMBR/rat A V L I W V V S V L L A      Majority
        390           400
L A V I W V G A L L L A      49.pep.4/29
I V S I W I L S F I L A      HumanETA.PEP
I V L I W V V S V L L A      HuETBR.PEP
L T L I W A V A I I V A      FROG.ET3R.PEP
A A F I W I I S M L L A      GRP-R
A V G I W V V S V L L A      NeuroMBR/rat
```

```
- - - - - - Y Q K A K S W    Majority
         440         450
V L A L T Y D S A R L W      49.pep.4/29
- - - - - Y Q D V K D W      HumanETA.PEP
- - - - - Y K T A K D W      HuETBR.PEP
- - - - - Y Q E V K V W      FROG.ET3R.PEP
- - - - - H P K I H S M      GRP-R
- - - - - H P K I H S V      NeuroMBR/rat N D H L K Q Q - - - R R      Majority
         490         500
T R G N K R Q I Q L E S      49.pep.4/29
S E H L K Q - - - - R R      HumanETA.PEP
N D H L K Q - - - - R R      HuETBR.PEP
N D H M K Q - - - - R R      FROG.ET3R.PEP
N I H V K Q I E S R K        GRP-R
N E H T K K Q M E T R K      NeuroMBR/rat

- - - - R S C E L - E I      Majority
         540         550
- - - - - - - - - - - M      49.pep.4/29
- M D K N R C E L - - -      HumanETA.PEP
- N D P N R C E L - - -      HuETBR.PEP
L K N K R S C I M A E I      FROG.ET3R.PEP
- - - - R S Y H Y S E V      GRP-R
- - - - R S F N Y K E I      NeuroMBR/rat K N C F N S C L C C C C      Majority
         590         600
S R A F M E C C C C C C      49.pep.4/29
K N C F Q S C L C C C C      HumanETA.PEP
K N C F K S C L C C W C      HuETBR.PEP
K N C F Q S C L C C W C      FROG.ET3R.PEP
R K Q F N T Q L L C C Q      GRP-R
R K H F N S Q L C C G Q      NeuroMBR/rat
```

Decoration 'Decoration #1': Shaded with solid residues that match the Consensus exactly.

```
     G T S L K S K A N D V X T D S - L N S G
         |                   |
        620                 630
     E Y T T E L E L S P F S A I R R E M S T
     G T S I Q W K N H D Q N N H - - - N T D
     Q S C L K F K A N D H G Y D - - - N F -
     G S G G K W K A N G H D L D L D R S S S
     M T S L K S T N P S V A T F S - L I N G
     M T S L K S N A K N V V T N S V L L N G
```

```
     R S S N K E S S S              Majority
         |
        640
     F A S V G T H C              49.pep.4/29
     R S S H K D S M N            HumanETA.PEP
     R S S N K Y S S S            HuETBR.PEP
     R L S N K Y S S S            FROG.ET3R.PEP
     N I C - H E R Y V            GRP-R
     H S T K Q E I A L            NeuroMBR/rat
```

HUMAN ENDOTHELIN-BOMBESIN RECEPTOR

This application is a Divisional of U.S. patent application Ser. No. 08/465,687 filed Jun. 6, 1995, now U.S. Pat. No. 5,750,370 which is entitled to priority benefits under 35 U.S.C. §120 for the information set forth therein, which is a Continuation-in-Part of PCT/US94/11843, filed Oct. 17, 1994.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human 7-transmembrane receptor. The transmembrane receptor is a G-protein coupled receptor. More particularly, the 7-transmembrane receptor has been putatively identified as an endothelin-bombesin receptor, sometimes hereinafter referred to as "ETBR." The invention also relates to inhibiting the action of such polypeptides.

It is well established that many medically significant biological processes are mediated by proteins participating in signal transduction pathways that involve G-proteins and/or second messengers, e.g., cAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46–50 (1987); Kobilka, B. K., et al., Science, 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The peptide endothelin is a peptide of 21 amino acid residues and performs in vivo effects via endothelin receptors. Endothelin (ET) is a peptide present in various tissues in animals and is known as a strong vasoconstrictor. ET is one peptide of a family of at least 4 mammalian peptides characterized by 2 disulphide bridges and 6 conserved amino acid residues at the C-terminus.

Members of the family are called endothelin-1 (ET-1), endothelin-2 (ET-2), and endothelin-3 (ET-3). A fourth peptide, vasointestinal contractor, is also sometimes described as the murine or rat form of ET-2. They differ mostly in the 29-membered ring system formed by the Cys-3-Cys-11 disulphide bond. Endothelins are produced by metabolism of a preproendothelin to a proendothelin, which is itself metabolized to the mature endothelin. The cleavage of proendothelin is thought to be due to the activity of a specific enzyme. ETs are distributed in a wide variety of vascular and non-vascular tissues (PNAS, USA, 86:2863–2867 (1989)).

It has previously been shown in vivo that ET-1 and ET-2 are much stronger vasoconstrictors than ET-3, whereas the three ET isopeptides are roughly equipotent in producing the transient vasodilation. The analysis of nucleic acid sequences of ETs has revealed that various kinds of ET isopeptides exist. These ET isopeptides are also different in their properties. Therefore, it appears that various sub-types of ET-receptors exist. The existence of various sub-types of ET-receptors has been proven by the radioactive ligand binding studies of Watanabe, H., et al., Biochem-Biophys, Res. Commun., 161:1252–1259 (1989), and Martin, E. R., et al., J. Biol. Chem., 265:14044–14049 (1990). These studies indicate the existence of at least two kinds of ET-receptors. One of them has a higher affinity for ET-1 and ET-2 than for ET-3 and the other has an affinity for ET-1, ET-2 and ET-3 with no cell activity. The ETA receptors have a lower affinity for ET-3 and the $ET_B$ receptors are non-selective.

The receptors are homologous to other heptahelical receptors of the rhodopsin superfamily, having 7 hydrophobic regions predicted to form transmembrane helices.

The placenta has a very high expression of both receptors, as does the lung. In general the non-selective $ET_B$ receptor seems to be more widely expressed (e.g., in liver, kidney and uterus) and is probably the more prominent receptor in the CNS, a result that agrees with binding and functional studies. The heart is the only tissue about which there is a consensus that an $ET_A$-type receptor predominates. The $ET_A$ receptors are associated with blood vessels and $ET_B$ receptors with glial, epithelial and ependymal cells, but few, if any, are associated with neurons. In the kidney, $ET_A$ receptors are located on blood vessel smooth-muscle cells, and $ET_B$ receptor expression occurs on a glomerular endothelium, vasa recti and the thin segments of Henle's loops.

Endothelins elicit biological responses by various signal transduction mechanisms, including the G-protein-coupled activation of phospholipase C and the activation of voltage-dependent $Ca^{2+}$ channels (Kasuya, Y., et al., Biochem. Biophys. Res. Commun., 61:1049–1055 (1989)). Thus, different sub-types of the endothelin receptor may use different signal-transduction mechanisms. Endothelin receptors have a relatively long N terminus preceding transmembrane segment I, and this portion may be involved in binding a relatively large endothelin peptide.

Applicants have discovered a G-protein coupled receptor which has hydropathicity and amino acid homology which shows the existence of the 7 hydrophobic segments and a significant sequence similarity with other G-protein-coupled receptors. The 7 membrane-spanning domains and extracellular N-terminus and cytoplasmic C-terminus have also been identified.

The G-protein coupled receptor of the present invention has been putatively identified as an endothelin-bombesin receptor as a result of its homology to the known endothelin receptors $ET_A$ and $ET_B$ and as a result of its ability to bind endothelin and bombesin.

In accordance with one aspect of the present invention, there is provided a novel putative mature polypeptide which is a G-protein coupled receptor, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptides by recombinant techniques.

In accordance with yet a further aspect of the present invention, there is provided a process for utilizing such polypeptides, or polynucleotides encoding such polypeptides for therapeutic purposes, to measure the concentration of endothelin in vivo, or in soluble form as an antagonist.

In accordance with yet a further aspect of the present invention, there are provided antibodies against such polypeptides.

In accordance with yet another aspect of the present invention, there are provided antagonists to such polypeptides, which may be used to inhibit the action of such polypeptides.

In accordance with still another embodiment, there is provided a process for using the receptor to screen for receptor antagonists and/or receptor agonists and/or receptor ligands.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1H, collectively, illustrate the cDNA sequence (SEQ ID NO:1) and the corresponding deduced amino acid sequence (SEQ ID NO:2) of the G-protein coupled receptor of the present invention. The first 26 amino acids represent a putative signal sequence. The standard one-letter abbreviation for amino acids is used.

Figure 3A1:
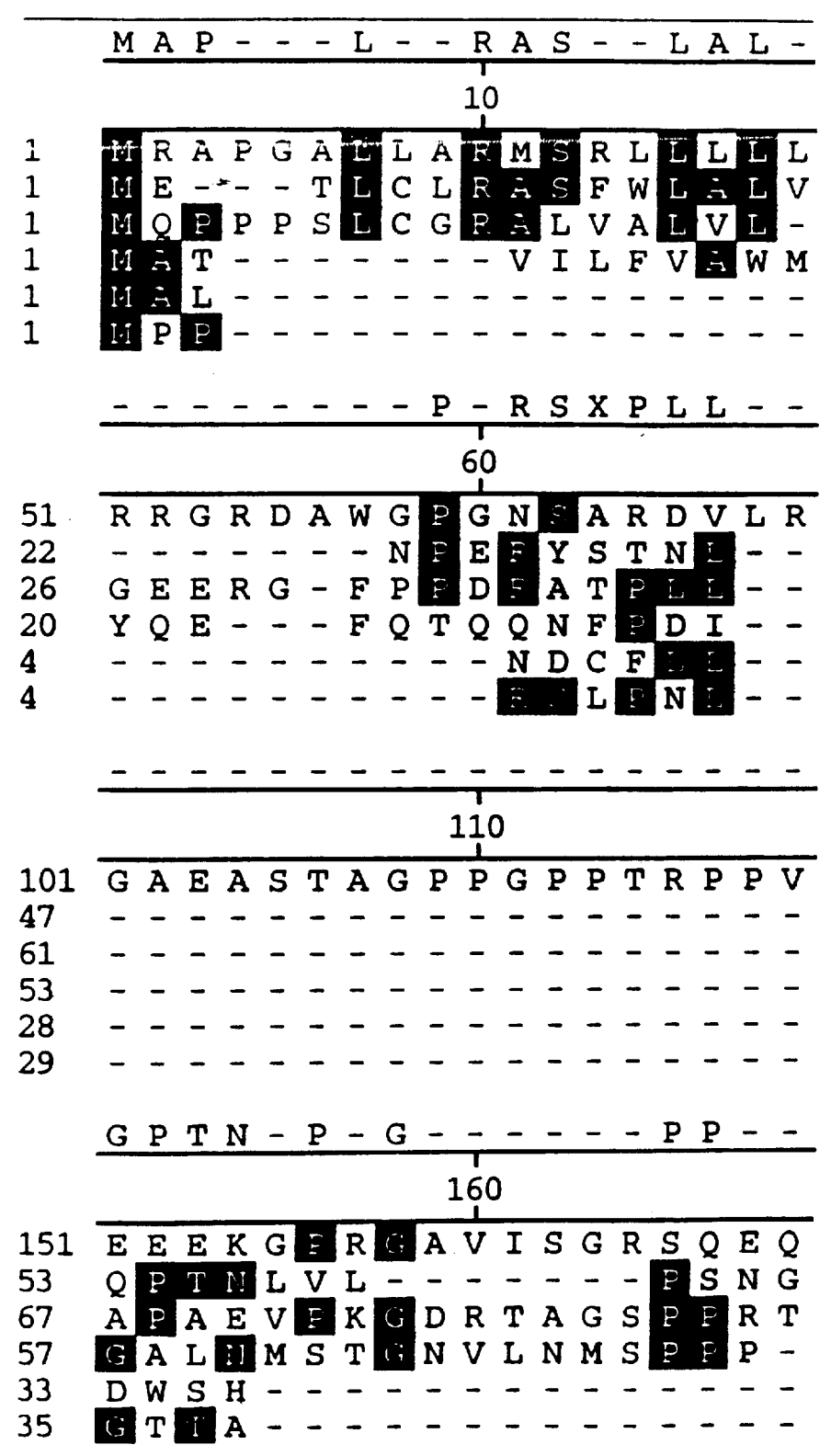
Figure 3A2:
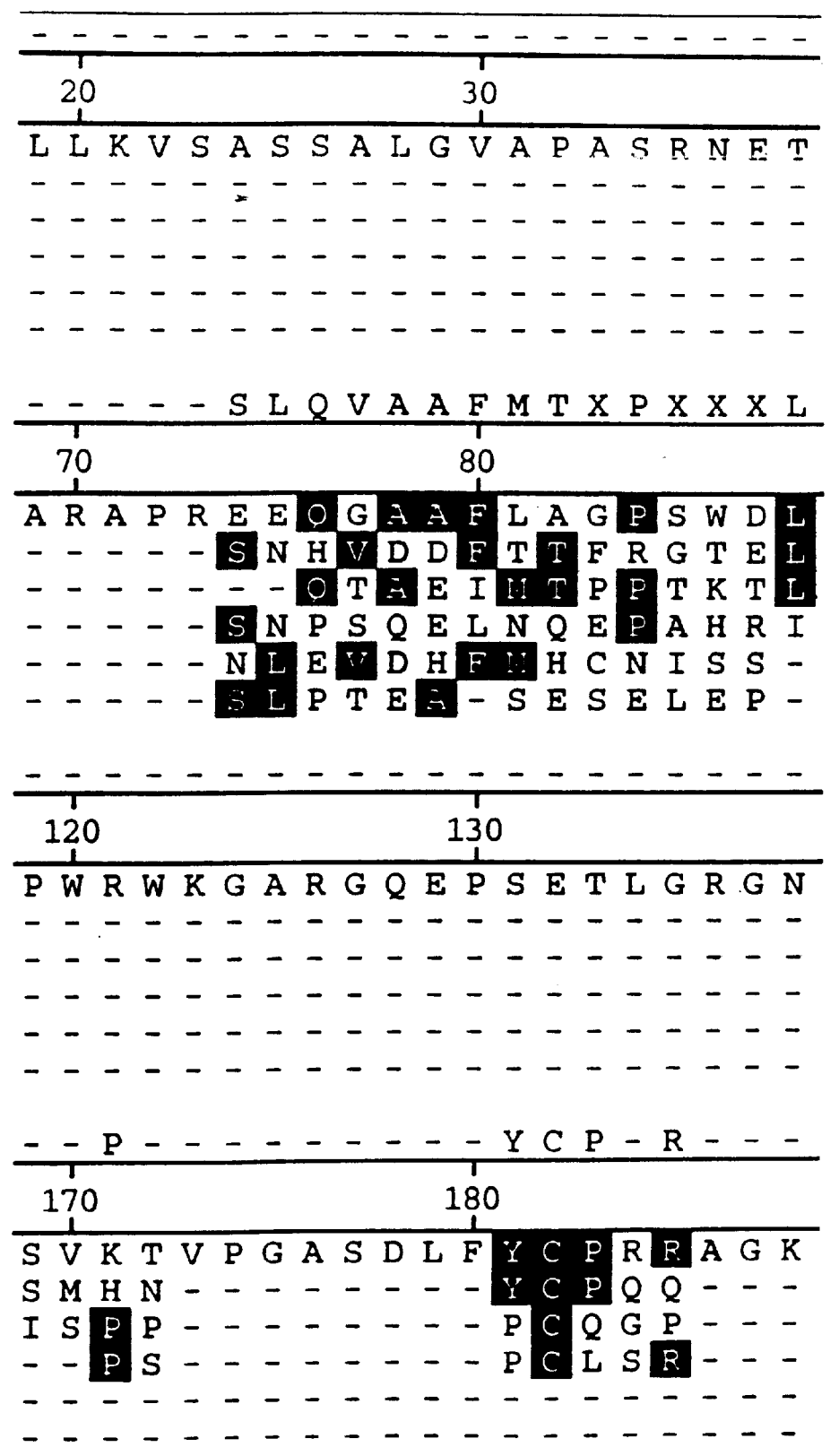
Figure 3B1:
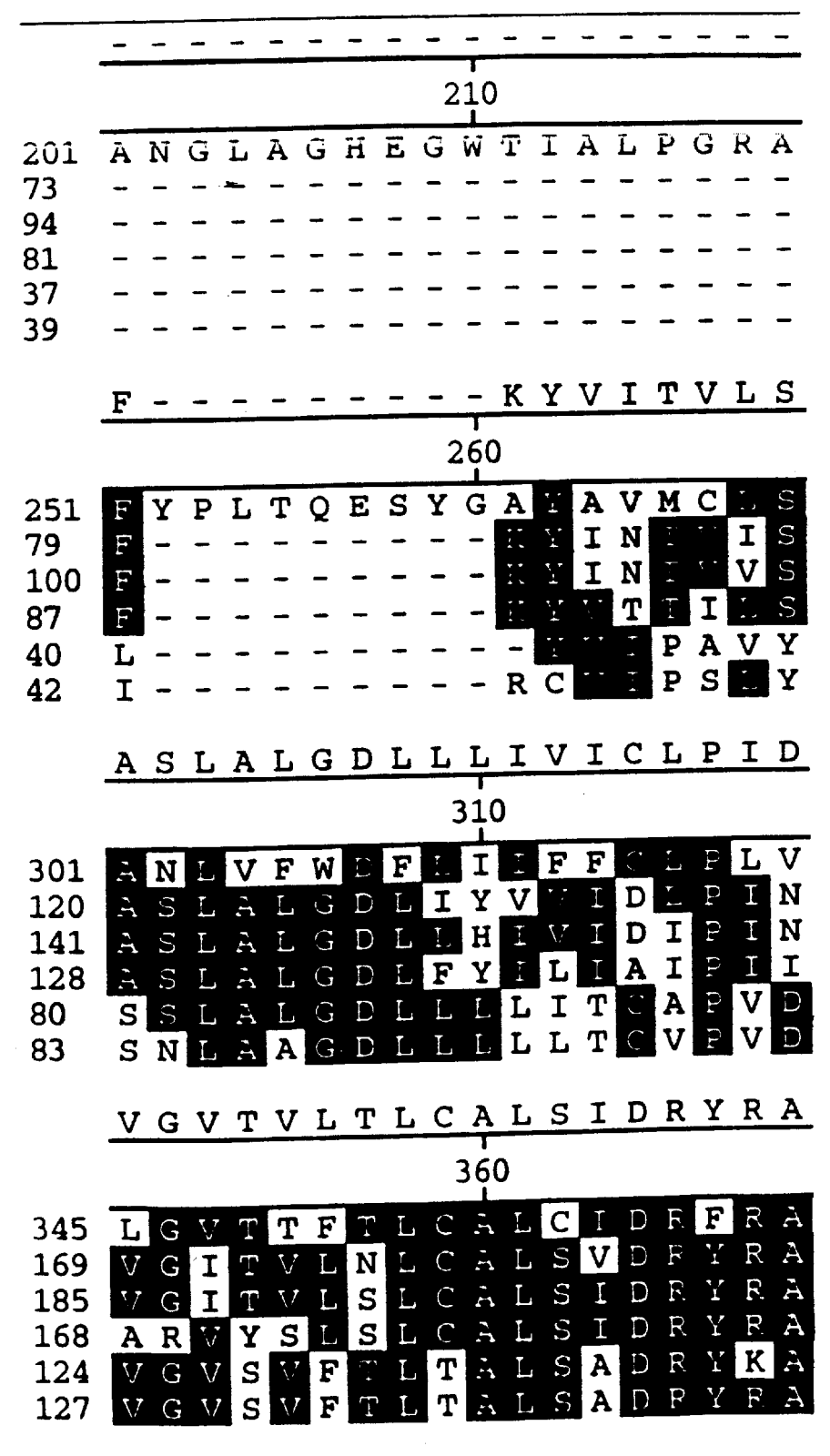
Figure 3B2:
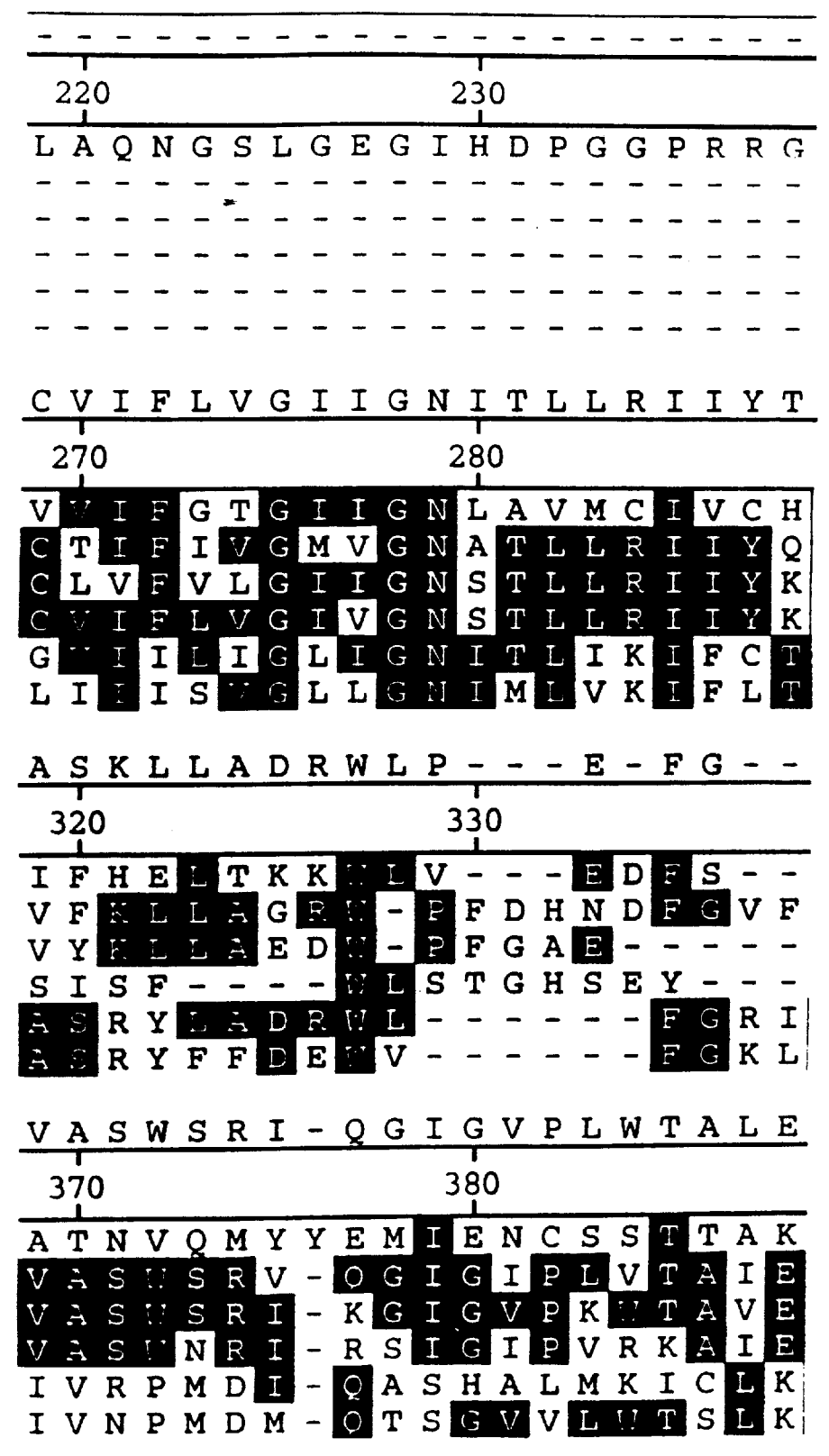
Figure 3C1:
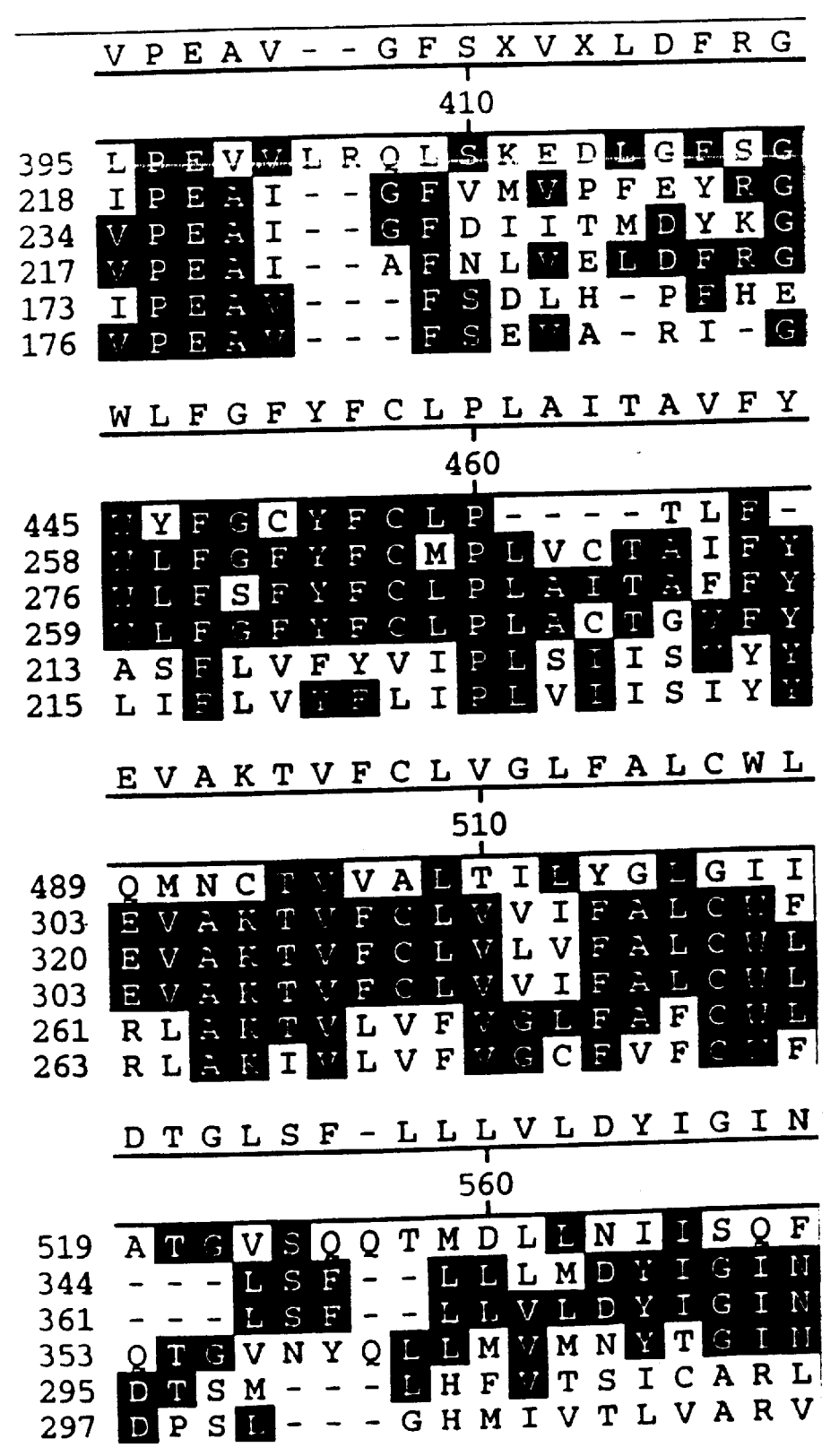
Figure 3C2:
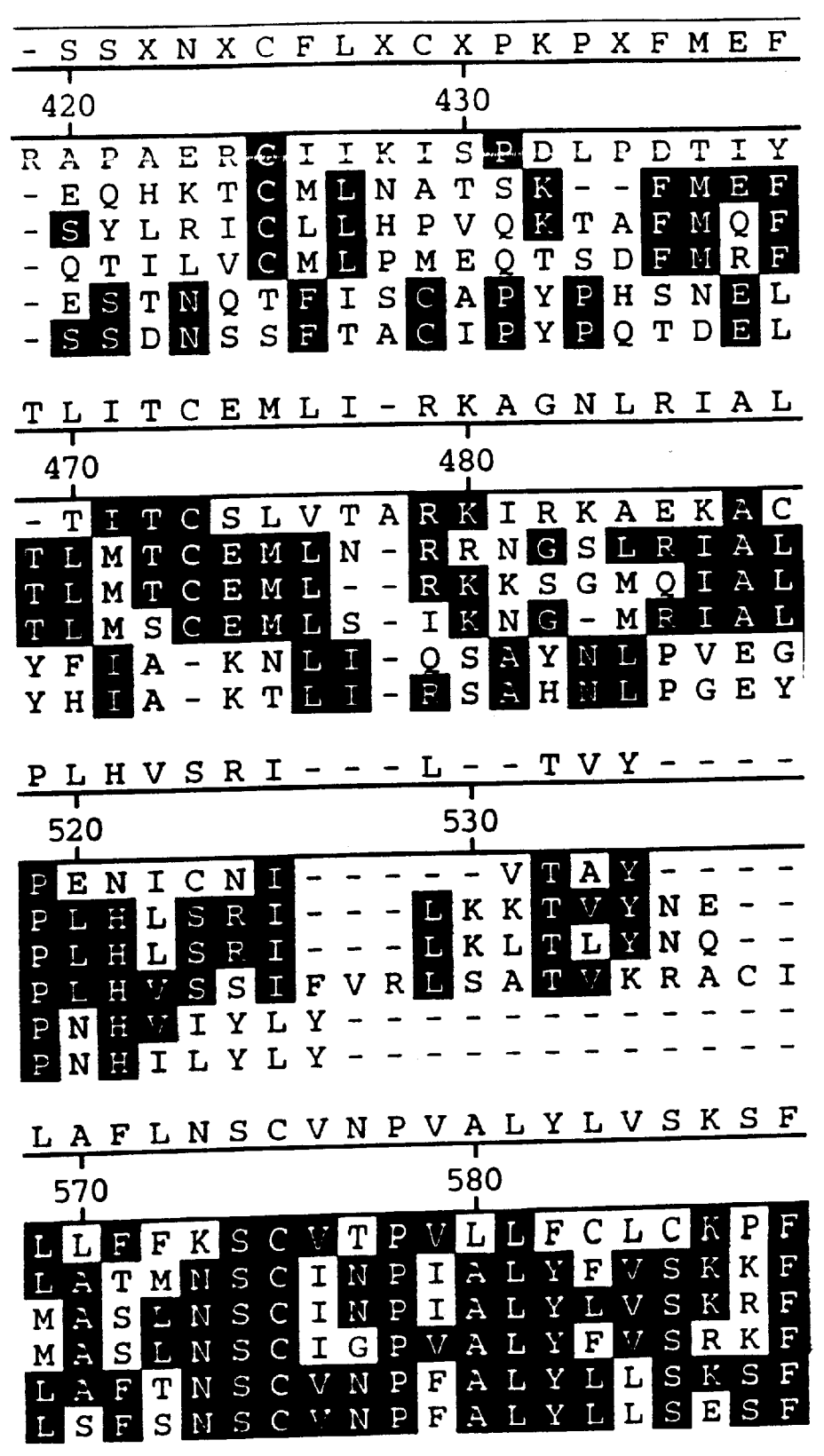
Figure 3D:
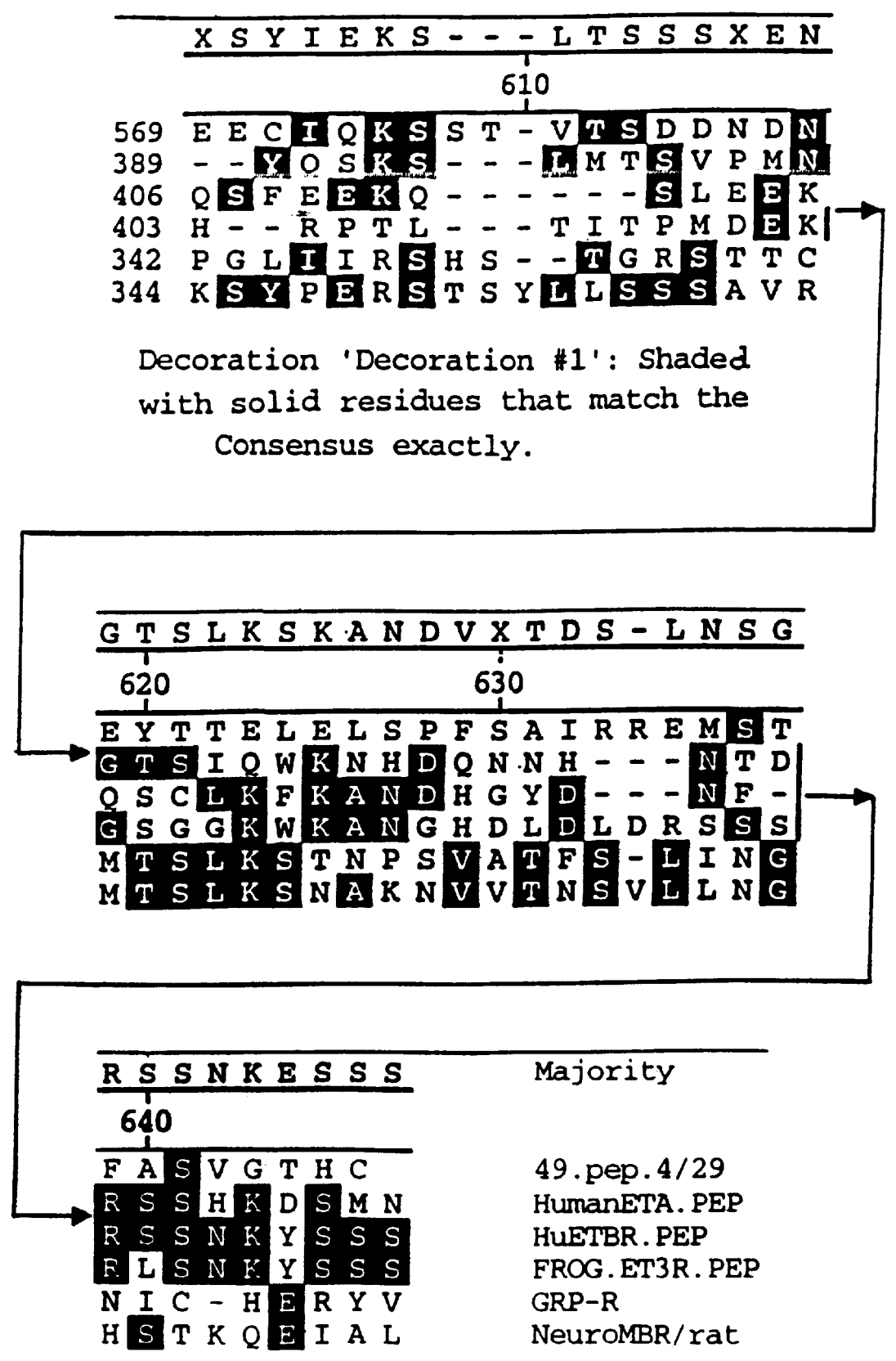

FIGS. 3A1–3A3, 3B1–3B3, 3C1–3C3, and 3D, collectively, illustrates an amino acid alignment of the G-protein coupled receptor of the present invention and endothelin receptors from various species of animals. Faded areas are those areas which match with the other amino acid sequences in the figure.

Figure 2A:
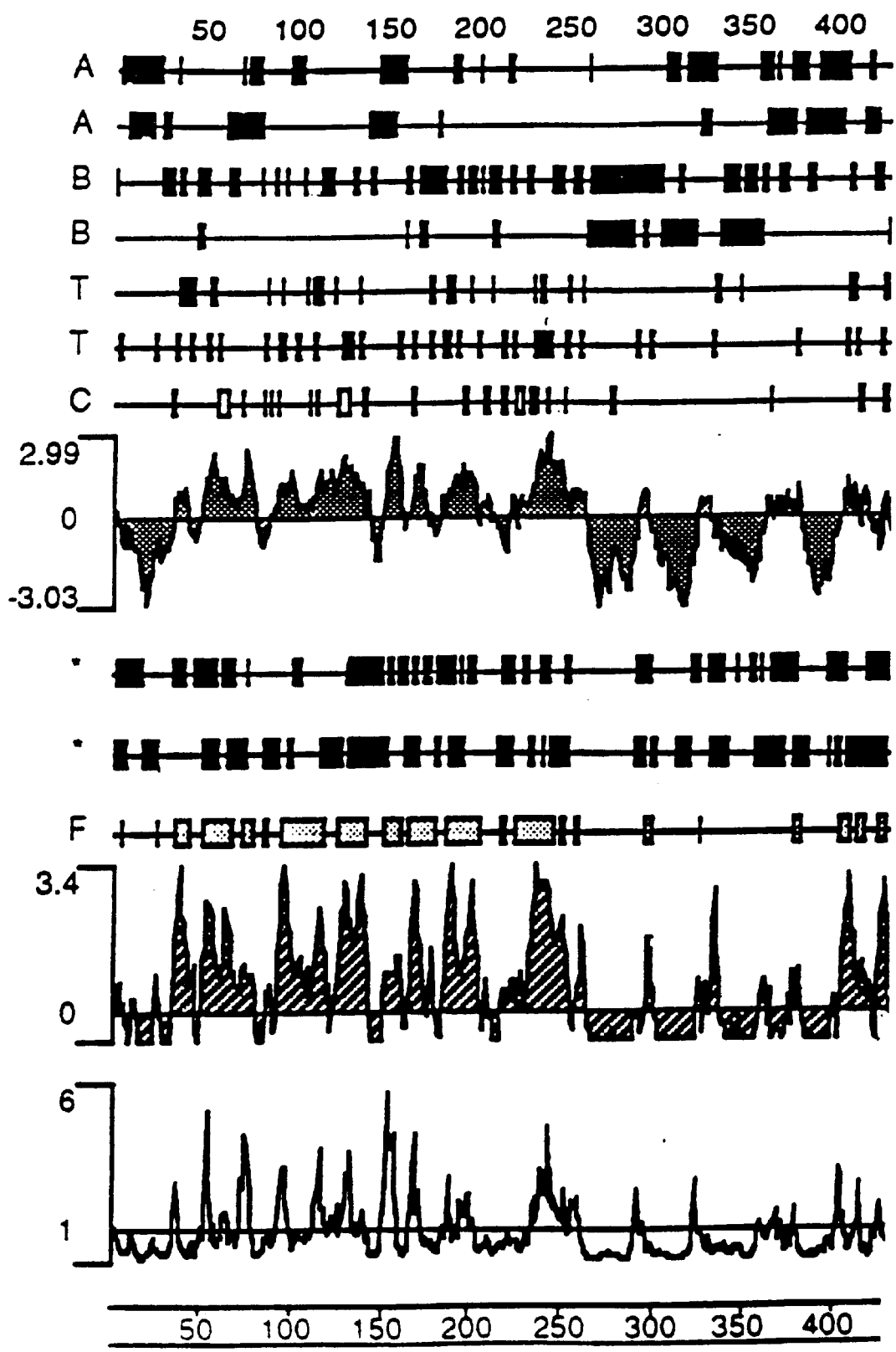
FIGS. 2A and 2B are an illustration of the secondary structural features of the G-protein coupled receptor. The first 7 illustrations set forth the regions of the amino acid sequence which are alpha helices, beta sheets, turn regions or coiled regions. The boxed areas are the areas which correspond to the region indicated. The second set of figures illustrate areas of the amino acid sequence which are exposed to intracellular, cytoplasmic or are membrane-spanning. The hydrophilicity part illustrates areas of the protein sequence which are the lipid bilayer of the membrane and are, therefore, hydrophobic, and areas outside the lipid bilayer membrane which are hydrophilic. The antigenic index corresponds to the hydrophilicity plot, since antigenic areas are areas outside the lipid bilayer membrane and are capable of binding antigens. The surface probability plot further corresponds to the antigenic index and the hydrophilicity plot. The amphipathic plots show those regions of the 13 sequences which are polar and non-polar. The flexible regions correspond to the second set of illustrations in the sense that flexible regions are those which are outside the membrane and inflexible regions are transmembrane regions.
Figure 2B:
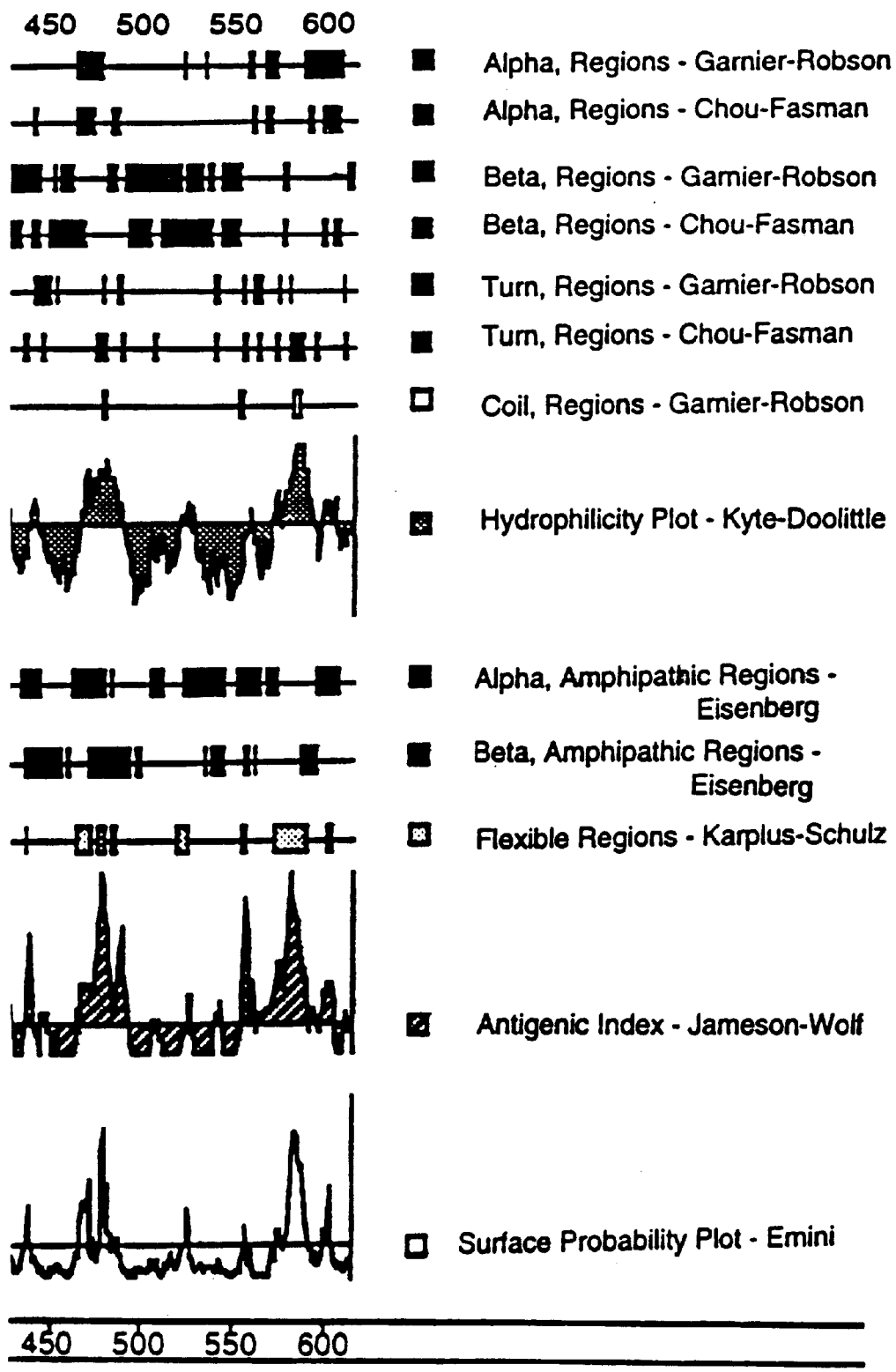

It should be pointed out that sequencing inaccuracies are a common problem which occurs in polynucleotide sequences. Accordingly, the sequence of the drawing is based on several sequencing runs and the sequencing accuracy is considered to be at least 97%.

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75823 with the ATCC, American Type Culture Collection, 10801 University Boulevard, Manassas, Va. 20110-2209 on Jun. 24, 1994. Since the strain referred to is being maintained under the terms of the Budapest Treaty, it will be made available to a patent office signatory to the Budapest Treaty.

A polynucleotide encoding a polypeptide of the present invention may be found in brain, liver and placenta. The polynucleotide of this invention was discovered in a cDNA library derived from a human brain. It is structurally related to the G protein-coupled receptor family. It contains an open reading frame encoding a protein of about 613 amino acid residues of which approximately the first 26 amino acids residues are the putative leader sequence such that the mature protein comprises 587 amino acids. The protein exhibits the highest degree of homology to a human $ET_A$ receptor with 30% identity and 55% similarity over a 420 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIGS. 1A–1H, collectively, (SEQ ID NO:1) or the deposited cDNA.

The polynucleotide which encodes for the mature polypeptide of FIGS. 1A–1H, collectively, (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1

(SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a G-protein coupled receptor polypeptide which has the deduced amino acid sequence of FIGS. 1A–1H, collectively, (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–1H, collectively, (SEQ ID NO:2) or that encoded by the deposited cDNA, means a polypeptide which either retains substantially the same biological function or activity as such polypeptide, i.e. functions as a G-protein coupled receptor, or retains the ability to bind the ligand or the receptor even though the polypeptide does not function as a G-protein coupled receptor, for example, a soluble form of the receptor. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which are employed for purification of the mature polypeptide or a proprotein sequence or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the ETBR genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli,* Streptomyces, *Salmonella typhimurium;* fungal cells, such as yeast; insect cells such as Drosophila and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9

(Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein coupled receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Bombesin, in addition to endothelin, has been found to bind to and stimulate the receptor of the present invention. Bombesin is a tetradecapeptide which has as a mammalian homolog the 27-amino acid peptide gastrin-releasing peptide (GRP). Bombesin is regarded as one of the most potent peptide to affect the central nervous system, since it has been reported as a thermoregulator in the rat (Brown, M. et al., Science, 196:998–1000 (1977)). Also, bombesin/gastrin releasing peptide is synthesized and secreted by small cell lung cancers (Davis, T. P. et al., Peptides, 13:401–17 (1992)).

The G-protein coupled receptor of the present invention may be employed in a process for screening for agonists and/or antagonists for the receptor.

In general, such screening procedures involve providing appropriate cells which express the receptor on the surface thereof. In particular, a polynucleotide encoding the receptor of the present invention is employed to transfect cells to thereby express the G-protein coupled receptor. Such transfection may be accomplished by procedures as hereinabove described.

One such screening procedure involves the use of a melanophore which are transfected to express the G-protein coupled receptor of the present invention. Such a screening technique is described in PCT WO 92/01810 published Feb. 6, 1992.

Thus, for example, such assay may be employed for screening for a receptor antagonist by contacting the melanophore cells which encode the G-protein coupled receptor with both the receptor ligand and a compound to be screened. Inhibition of the signal generated by the ligand indicates that a compound is a potential antagonist for the receptor, i.e., inhibits activation of the receptor.

The screen may be employed for determining an agonist by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, potential agonists or antagonists may be contacted with a cell which expresses the G-protein coupled receptor and a second messenger response, e.g. signal transduction or pH changes, may be measured to determine whether the potential agonist or antagonist is effective.

Another such screening technique involves introducing RNA encoding the G-protein coupled receptor into Xenopus oocytes to transiently express the receptor. The receptor oocytes may then be contacted with the receptor ligand and a compound to be screened, followed by detection of inhibition of a calcium signal.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening for an antagonist or agonist may be accomplished as hereinabove described by detecting activation of the receptor or inhibition of activation of the receptor from the phospholipase second signal.

Another method involves screening for antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a potential antagonist in the presence of a labeled form of a known ligand. The ligand can be labeled, e.g., by radioactivity. The amount of labeled ligand bound to the receptors is measured, e.g., by measuring radioactivity of the receptors. If the potential antagonist binds to the receptor as determined by a reduction of labeled ligand which binds to the receptors, the binding of labeled ligand to the receptor is inhibited.

In general, antagonists for G-protein coupled receptors which are determined by such screening procedures may be employed for a variety of therapeutic purposes. For example, such antagonists have been employed for treatment of hypertension, angina pectoris, myocardial infarction, ulcers, asthma, allergies, psychoses, depression, migraine, vomiting, and benign prostatic hypertrophy.

Agonists for G-protein coupled receptors are also useful for therapeutic purposes, such as the treatment of asthma, Parkinson's disease, acute heart failure, hypotension, urinary retention, and osteoporosis.

Examples of potential antagonists include an antibody, or in some cases an oligonucleotide, which binds to the G-protein coupled receptor but does not elicit a second messenger response such that the activity of the G-protein coupled receptor is prevented. Potential antagonists also include proteins which are closely related to the ligand of the G-protein coupled receptor, i.e. a fragment of the ligand, which have lost biological function and when binding to the G-protein coupled receptor, elicit no response.

A potential antagonist also includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of G-protein coupled receptor. The antisense RNA oligonucleotide hybridizes to the mRNA in vivo and blocks translation of the mRNA molecule into the G-protein coupled receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptor.

Another potential antagonist is a small molecule which binds to the G-protein coupled receptor, making it inaccessible to ligands such that normal biological activity is prevented. Examples of small molecules include but are not limited to small peptides or peptide-like molecules.

Potential antagonists also include a soluble G-protein coupled receptor, e.g. a fragment of the receptor, which binds to the ligand and prevents the ligand from interacting with membrane bound G-protein coupled receptors.

An endothelin antagonist may be employed to offset the vasoconstrictive effects of endothelin and, therefore, may be employed to treat hypertension through vasodilation. These antagonists may also be used to treat the long-lasting vasospasms due to subarachnoid hemorrhages which cause increases in endothelin levels in cerebrospinal fluid and plasma.

Endothelin antagonists may also be employed to treat ulcerogenesis and gastric lesions. ET-1 and ET-3 induce gastric lesions and enhance alcohol-induced lesions. Accordingly, inhibiting ET-1 and ET-3 from interacting with the ETBRs can prevent these conditions.

Endothelins potently contract pulmonary smooth muscle and levels of endothelins are increased in pulmonary lavage fluid during asthmatic attacks, therefore, antagonists for diminishing or preventing binding of endothelin may be employed to treat asthma.

Endothelin levels are increased in cancer tissue and a cancer-derived cell line can be stimulated to produce endothelin. ET-1 itself stimulates growth of cancerous cells. Accordingly, endothelin antagonists may be employed to prevent the growth of cancer cells and tumors.

An increase in circulating endothelin levels is increased by ciclosporin, which may explain the toxic effects of ciclosporin. Accordingly, endothelin antagonists may be used to prevent and/or treat ciclosporin toxicity.

Endothelin antagonists may also be employed to treat septic shock which is caused by pathological levels of endothelins. Further, hypertension, congestive heart failure, coronary artery disease, atherosclerosis, restenosis, benign prostatic hypertrophy, renal failure and stroke may also be treated with the antagonist of ETBRs.

Bombesin antagonists may be employed to treat small cell lung cancers which synthesize and secret bombesin/gastrin releasing peptide. A bombesin antagonist will prevent bombesin from stimulating the ETBR of the present invention.

The antagonists may be employed in a composition with a pharmaceutically acceptable carrier, e.g., as hereinafter described.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

The ETBR polypeptides and antagonists or agonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides and agonists and antagonists may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The ETBR polypeptides and antagonists or agonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques,* Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy, Vol.* 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

This invention also provides a method of detecting expression of a receptor polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a receptor polypeptide of the present invention, by low stringency cross hybridization, or by identifying receptors that interact with related natural or synthetic ligands and or elicit similar behaviors after genetic or pharmacological blockade of the receptor polypeptides of the present invention.

The present invention also contemplates the use of the genes of the present invention as a diagnostic, for example, some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., calorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature,* 324:163–166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA,* 85:4397–4401 1985).

The sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 ìg of plasmid or DNA fragment is used with about 2 units of enzyme in about 20 ìl of buffer solution. For the purpose of isolating DNA fragments for plasmid construction, typically 5 to 50 ìg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of ETBR

The DNA sequence encoding for ETBR, ATCC #75823, is initially amplified using PCR oligonucleotide primers corresponding to the 5' and sequences of the processed ETBR protein (minus the signal peptide sequence) and the vector sequences 3' to the ETBR gene. Additional nucleotides corresponding to ETBR were added to the 5' and 3' sequences respectively. The 5' oligonucleotide primer has the sequence 5' CACTAAGCTTAATGCGAGC-CCCGGGCGCG 3' (SEQ ID NO:3) contains a HindIII restriction enzyme site followed by 18 nucleotides of ETBR coding sequence starting from the presumed terminal amino acid of the processed protein codon. The 3' sequence 5' GAACTTCTAGACCGTCAGCAATGAGTACCGAC 3' (SEQ ID NO:4) contains complementary sequences to an XbaI site and is followed by 18 nucleotides of ETBR. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with HindIII and XbaI. The amplified sequences were ligated into pQE-9 and were inserted in frame with the sequence encoding for the histidine tag and the RBS. The ligation mixture was then used to transform E. coli HB101 by the procedure described in Sambrook, J. et al., Molecular Cloning: A Laboratory Manual, Cold Spring Laboratory Press, (1989). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized ETBR was purified from this solution by chromatography on a Nickel-Chelate column under conditions that allow for tight binding by proteins containing the 6-His tag (Hochuli, E. et al., J. Chromatography 411:177–184 (1984)). ETBR was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Expression of Recombinant ETBR in COS cells

The expression of plasmid, pETBR HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire ETBR protein and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for ETBR, ATCC #75823, was constructed by PCR on the original EST cloned using two primers: the 5' primer 5' GTCCAAGCTTGCCACCAT-GCGAGCCCCGGGCGCG 3' (SEQ ID NO:5) contains a HindIII site followed by 18 nucleotides of ETBR coding sequence starting from the initiation codon; the 3' sequence 5' CTAGCTCGAGTCAAGCGTAGTCTGG-GACGTCGTATGGGTAGCAGCAAT GAGTTCCGA-CAGA 3' (SEQ ID NO:6) contains complementary sequences to an XhoI site, translation stop codon, HA tag and the last 18 nucleotides of the ETBR coding sequence (not including the stop codon). Therefore, the PCR product contains a HindIII site, ETBR coding sequence followed by HA tag fused in frame, a translation termination stop codon next to the HA tag, and an XhoI site. The PCR amplified DNA fragment and the vector, pcDNAI/Amp, were digested with HindIII and XhoI restriction enzyme and ligated. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant ETBR, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the ETBR HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Cloning and Expression of ETBR Using the Baculovirus Expression System

The DNA sequence encoding the full length ETBR protein, ATCC #75823, amplified using PCR oligonucleotide primers corresponding to the 5' and 3' sequences of the gene:

The 5' primer has the sequence 5'CGGGATCCGCCACC ATGCGAGC CCCGGGCGCG 3' (SEQ ID NO:7) and contains a BamHI restriction enzyme site (in bold) followed by 6 nucleotides resembling an efficient signal for the initiation of translation in eukaryotic cells (J. Mol. Biol. 1987, 196, 947–950, Kozak, M.), and just behind, is the first 18 nucleotides of the ETBR gene (the initiation codon for translation "ATG" is underlined).

The 3' primer has the sequence 5'CGGGATCCCGCT-CAGCAA TGAGTTCCGAC 3' (SEQ ID NO:8) and contains the cleavage site for the restriction endonuclease BamHI and 18 nucleotides complementary to the 3' non-translated sequence of the ETBR gene. The amplified sequences were isolated from a 1% agarose gel using a commercially available kit ("Geneclean," BIO 101 Inc., La Jolla, Calif.). The fragment was then digested with the endonucleases BamHI and then purified again on a 1% agarose gel. This fragment is designated F2.

The vector pRG1 (modification of pVL941 vector, discussed below) is used for the expression of the ETBR protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and then dephosphorylated using calf intestinal phosphatase by procedures known in the art. The DNA was then isolated from a 1% agarose gel. This vector DNA is designated V2.

Fragment F2 and the dephosphorylated plasmid V2 were ligated with T4 DNA ligase. E. coli HB101 cells were then transformed and bacteria identified that contained the plasmid (pBacETBR) with the ETBR gene using the enzymes BamHI. The sequence of the cloned fragment was confirmed by DNA sequencing.

5 µg of the plasmid pBacETBR were cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBacETBR were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses were added to the cells and blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-ETBR at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 4

Xenopus Oocyte Assay to Identify Ligand

RNA was synthesized in vitro from linearized DNA, ATCC #75823, using an RNA transcription kit. This RNA was microinjected into Xenopus oocytes (10 ng of RNA/ oocytes). The oocytes were manually defolliculated prior to microinjection to remove any endogenous receptors that might be present in the follicular membranes. The injected oocytes were maintained in modified Barth's medium at 18° C. for 48 hours to allow for receptor protein expression. Electrophysiology was performed using the voltage-clamp technique. Oocytes were clamped at −60 mV and the calcium activated chloride channel activity was recorded in Barth's medium at room temperature. Data were analyzed using Axotape software.

Figure 4:
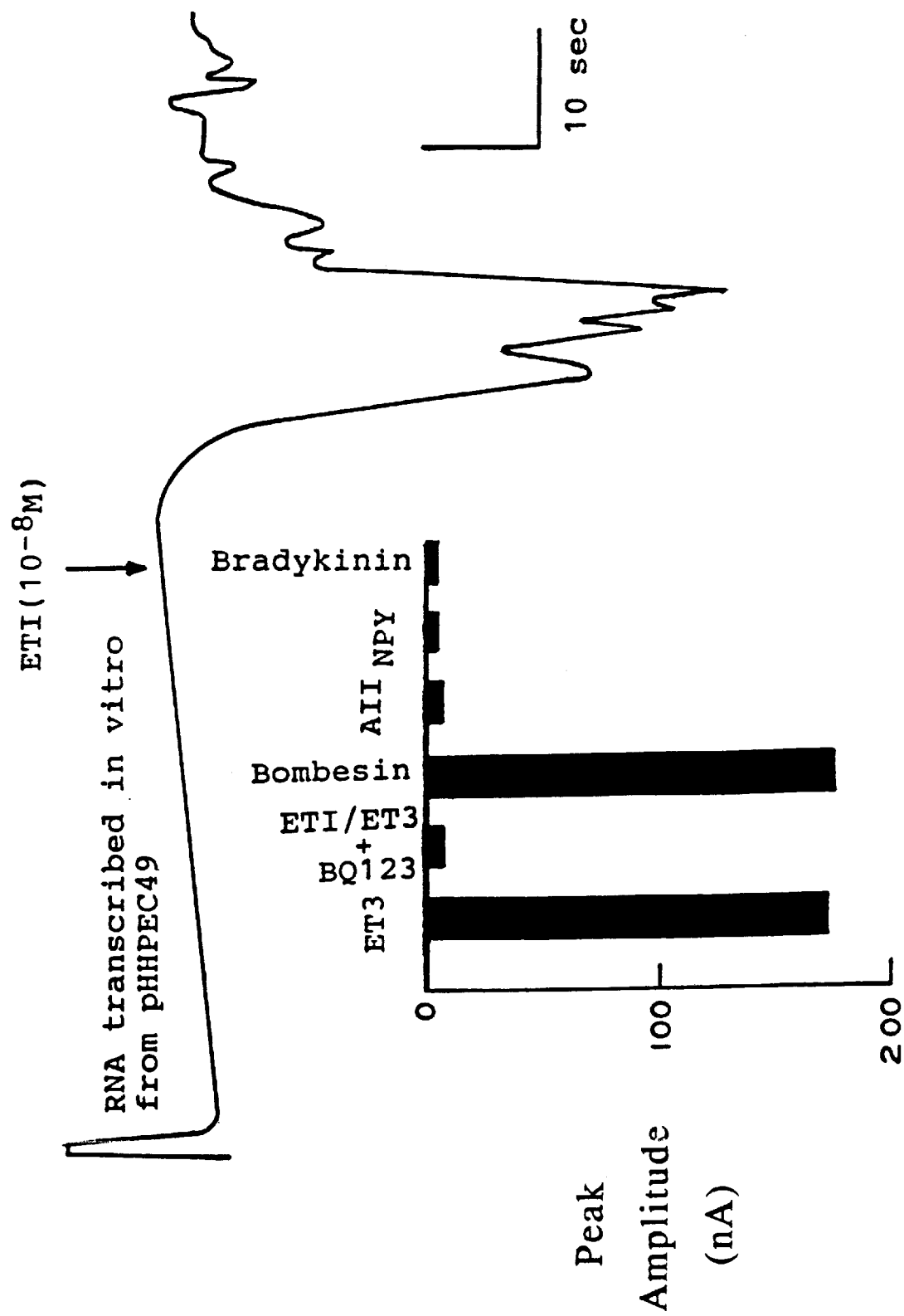
FIG. 4 shows that ET1, ET3 and Bombesin induced chloride currents in oocytes injected with pHHPEC49 derived RNA transcripts. The trace shows ET1 mediated chloride current (nanoamps). Arrow indicates ET1 addition. The inset shows the mean peak responses to 10 nM AII, Neuropeptide Y (NPY) and Bradykinin. The mean peak±S.E. peak current response to ET1 is 150±50 (n=75), ET2 156±55 (n=75) and Bombesin 148±47 (n=75).

As shown in FIG. 4, oocytes injected with the synthetic RNA complementary to DNA from ATCC #75823, illicited fairly strong Cl$^-$ currents upon addition of 10 nM ET1, ET3 as well as Bombesin. Addition of ET1, ET3 and Bombesin to uninjected oocytes on the other hand did not elicit any change in membrane potential (data not shown). The ET1 and ET3 mediated response was blocked by the ET receptor peptide antagonist BQ123. Addition of related peptide ligands like AII, Neuropeptide Y and Bradykinin did not illicit any response (FIG. 4). This indicates that the ETBR is functional and is capable of coupling to a second messenger system which leads to the mobilization of intercellular stores of calcium via production of inositol triphosphate. Since it responds to both ET and Bombesin it represents a novel endothelin-bombesin receptor.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated protein molecule comprising an amino acid sequence selected from the group consisting of:
   (a) a mature polypeptide produced from the protein as set forth in SEQ ID NO:2;
   (b) a mature polypeptide produced from the protein encoded by the cDNA contained in ATCC Deposit No. 75823;
   (c) amino acids −26 to +587 of SEQ ID NO:2; and
   (d) the full length amino acid sequence encoded by the cDNA contained in ATCC Deposit No.75823.

2. The isolated protein molecule of claim 1, wherein said amino acid sequence is (a).

3. The isolated protein molecule of claim 2, wherein said amino acid sequence comprises amino acids +1 to +587 of SEQ ID NO:2.

4. An isolated protein produced by the method comprising:
   (a) culturing a host cell comprising a heterologous promoter operably associated with a polynucleotide encoding the protein molecule of claim 2 under conditions suitable to produce said protein molecule; and
   (b) recovering said protein molecule.

5. The isolated protein molecule of claim 1, wherein said amino acid sequence is (b).

6. An isolated protein produced by the method comprising:
   (a) culturing a host cell comprising a heterologous promoter operably associated with a polynucleotide encoding the protein molecule of claim 5 under conditions suitable to produce said protein molecule; and
   (b) recovering said protein molecule.

7. The isolated protein molecule of claim 1, wherein said amino acid sequence is (c).

8. An isolated protein produced by the method comprising:
   (a) culturing a host cell comprising a heterologous promoter operably associated with a polynucleotide encoding the protein molecule of claim 7 under conditions suitable to produce said protein molecule; and
   (b) recovering said protein molecule.

9. The isolated protein molecule of claim 1, wherein said amino acid sequence is (d).

10. An isolated protein produced by the method comprising:
    (a) culturing a host cell comprising a heterologous promoter operably associated with a polynucleotide encoding the protein molecule of claim 9 under conditions suitable to produce said protein molecule; and
    (b) recovering said protein molecule.

11. The isolated protein molecule of claim 1 further comprising a heterologous polypeptide.

12. A composition comprising the protein molecule of claim 1 and a pharmaceutical carrier.

13. An isolated protein molecule comprising an amino acid sequence selected from the group consisting of:
    (a) at least 30 contiguous amino acids as set forth in SEQ ID NO:2 or encoded by the human cDNA contained in ATCC Deposit No. 75823;
    (b) an amino acid sequence encoded by at least 30 contiguous nucleotides of the coding region of SEQ ID NO:1;
    (c) a protein fragment of the amino acid sequence of SEQ ID NO:2, wherein said fragment binds endothelin;
    (d) a protein fragment encoded by the human cDNA contained in ATCC Deposit No. 75823, wherein said fragment binds endothelin;
    (e) a protein fragment of the amino acid sequence of SEQ ID NO:2, wherein said fragment binds bombesin; and
    (f) a protein fragment encoded by the human cDNA contained in ATCC Deposit No. 75823, wherein said fragment binds bombesin.

14. The isolated protein molecule of claim 13, wherein said amino acid sequence is (a).

15. An isolated protein produced by the method comprising:
    (a) culturing a host cell comprising a heterologous promoter operably associated with a polynucleotide encoding the protein molecule of claim 14 under conditions suitable to produce said protein molecule; and
    (b) recovering said protein molecule.

16. The isolated protein molecule of claim 13, wherein said amino acid sequence is (b).

17. The isolated protein molecule of claim 16, wherein said amino acid sequence comprises at least 50 contiguous amino acids as set forth in SEQ ID NO:2 or encoded by the human cDNA contained in ATCC Deposit No. 75823.

18. The isolated protein molecule of claim 17, wherein said amino acid sequence comprises amino acids −25 to +587 of SEQ ID NO:2.

19. An isolated protein produced by the method comprising:
    (a) culturing a host cell comprising a heterologous promoter operably associated with a polynucleotide encoding the protein molecule of claim 16 under conditions suitable to produce said protein molecule; and
    (b) recovering said protein molecule.

20. The isolated protein molecule of claim 13, wherein said amino acid sequence is (c).

21. The isolated protein molecule of claim 20, wherein said amino acid sequence is encoded by at least 50 contiguous nucleotides of SEQ ID NO:1 or the human cDNA in ATCC Deposit No. 75823.

22. An isolated protein produced by the method comprising:

(a) culturing a host cell comprising a heterologous promoter operably associated with a polynucleotide encoding the protein molecule of claim 20 under conditions suitable to produce said protein molecule; and (b) recovering said protein molecule.

23. The isolated protein molecule of claim 13, wherein said amino acid sequence is (d).

24. An isolated protein produced by the method comprising:

(a) culturing a host cell comprising a heterologous promoter operably associated with a polynucleotide encoding the protein molecule of claim 23 under conditions suitable to produce said protein molecule; and (b) recovering said protein molecule.

25. The isolated protein molecule of claim 13, wherein said amino acid sequence is (e).

26. An isolated protein produced by the method comprising:

(a) culturing a host cell comprising a heterologous promoter operably associated with a polynucleotide encoding the protein molecule of claim 15 under conditions suitable to produce said protein molecule; and (b) recovering said protein molecule.

27. The isolated protein molecule of claim 13, wherein said amino acid sequence is (f).

28. An isolated protein produced by the method comprising:

(a) culturing a host cell comprising a heterologous promoter operably associated with a polynucleotide encoding the protein molecule of claim 27 under conditions suitable to produce said protein molecule; and (b) recovering said protein molecule.

29. The isolated protein molecule of claim 13 further comprising a heterologous polypeptide.

30. A composition comprising the protein molecule of claim 13 and a pharmaceutical carrier.

31. An isolated protein molecule comprising an amino acid sequence selected from the group consisting of:

(a) amino acids +9 to +18 of SEQ ID NO:2;

(b) amino acids +22 to +51 of SEQ ID NO:2;

(c) amino acids +64 to +92 of SEQ ID NO:2;

(d) amino acids +94 to +114 of SEQ ID NO:2;

(e) amino acids +122 to +132 of SEQ ID NO:2;

(f) amino acids +136 to +145 of SEQ ID NO:2;

(g) amino acids +155 to +176 of SEQ ID NO:2;

(h) amino acids +188 to +225 of SEQ ID NO:2;

(i) amino acids +376 to +394 of SEQ ID NO:2;

(j) amino acids +397 to +403 of SEQ ID NO:2;

(k) amino acids +441 to +466 of SEQ ID NO:2;

(l) amino acids +528 to +536 of SEQ ID NO:2;

(m) amino acids +538 to +563 of SEQ ID NO:2; and (n) amino acids +571 to +578 of SEQ ID NO:2.

32. The isolated protein molecule of claim 31 further comprising a heterologous polypeptide.

33. A composition comprising the protein molecule of claim 31 and a pharmaceutical carrier.

34. An isolated protein produced by the method comprising:

(a) culturing a host cell comprising a heterologous promoter operably associated with a polynucleotide encoding the protein molecule of claim 31 under conditions suitable to produce said protein molecule; and (b) recovering said protein molecule.

35. The isolated protein molecule of claim 31, wherein said amino acid sequence is (a).

36. The isolated protein molecule of claim 31, wherein said amino acid sequence is (b).

37. The isolated protein molecule of claim 31, wherein said amino acid sequence is (c).

38. The isolated protein molecule of claim 31, wherein said amino acid sequence is (d).

39. The isolated protein molecule of claim 31, wherein said amino acid sequence is (e).

40. The isolated protein molecule of claim 31, wherein said amino acid sequence is (f).

41. The isolated protein molecule of claim 31, wherein said amino acid sequence is (g).

42. The isolated protein molecule of claim 31, wherein said amino acid sequence is (h).

43. The isolated protein molecule of claim 31, wherein said amino acid sequence is (i).

44. The isolated protein molecule of claim 31, wherein said amino acid sequence is (j).

45. The isolated protein molecule of claim 31, wherein said amino acid sequence is (k).

46. The isolated protein molecule of claim 31, wherein said amino acid sequence is (l).

47. The isolated protein molecule of claim 31, wherein said amino acid sequence is (m).

48. The isolated protein molecule of claim 31, wherein said amino acid sequence is (n).

* * * * *

```
                         SEQUENCE LISTING (1) GENERAL INFORMATION:

(iii) NUMBER OF SEQUENCES:  8

(2) INFORMATION FOR SEQ ID NO:1:

(i) SEQUENCE CHARACTERISTICS:
        (A) LENGTH:  4156 BASE PAIRS
        (B) TYPE:  NUCLEIC ACID
        (C) STRANDEDNESS:  SINGLE
        (D) TOPOLOGY:  LINEAR (ii) MOLECULE TYPE:  cDNA (xi) SEQUENCE DESCRIPTION:  SEQ ID NO:1:

CCCACTATGT TGGCCAGGAT GGTCTTGATT TCTTGACCTC GTGTTCTGCC CGCCTCTACC      60

TCCCAAAGTG CCGGGATTAC AGGCGTGACT GCTGTGCCCG GCCCCAGCAT CACTTTTATA     120

GCTTTCTGTG CCTCTTCCTC TGGGCCTTGG TGTATGAAGC CACTTGCCTT TCTCTGTTGG     180

GAAGCGAGCA GAATCAGATT GCTACTCATG ATGCAGTCCG GGCAGGGCAT ACTGTCACCT     240

TTGGCTGTGG ACACAGTTGT CAGGATAGGG GAGAAGCCCT TTAGGTCCGT CTTCTTGACA     300

CAGCCCTCCT ACCTGGTTAC GCTGGTGCTT TCGCTTGGTT TAGACAACCA AGACACTTGA     360

GAATTATGCT GTCCTCAGAA TGTCTGATGA AAAGAACAGA TTCACTTTTT GGACACAATG     420

CCCATTAGCC ATCTTTGGCA GTGTTTCTGA TCAAAGGTTC CCCATGCCTG CTCTAGGAAA     480

GTAAACTTTT TTCAGAATAA ATCCTCAAAT GGATTACTGA GTAGTCTTTG CACCATTCCC     540

ATCAGCCTAA TCAGACTGAA TGGTCACGCT CAGTGCAAAA AGCTGTTTTG CTGTTAGGAT     600

GTTTCAGTGT TTCTTGTCTT TCCTGGAACA GTTCAGTTGT TTAAATTTAG TAATTCAATC     660

CTGACCAGTG TAAACCCACT TAATTATTGC AGCCTAAAGA ATTCAGCTAC TTCTACTCTT     720

CATAAATGTG CCCAAGTAAA TATGTGTTTT TAATATTCAA CCCTGGAAAA TTAGTAATTC     780

AGATGATAAA AGCTCATGTT TTGGTGTCTT TGTACTCAGA TTGTGAACAG GCATATTTCA     840

CTGATTTAGA CTTAGTATAC TTGATGAGAA TGCTCAGGTT GAAGAGATAG TTCTGTCAGC     900

AATCCAACAT CTATAGCAAT GTGGAAAAAG TAATCAACTC ATATTTCACG AATTTGATGT     960

ATGTTGTGAT TTAGAGGGCA TGAGATAAAG TTTATATTTG AACTGTGTGG GGTAGGGGGA    1020

AGAAGAGGTT GCTTAAGCAA ATGGGGGGGT GATTGAGGAA CAAGATGTCT CTAAGATGAG    1080

AAGTTATTTT CTTGCATCAT AGAAGCACTC TCTCCACCCG GGAGTGATTG TGTTAACTAT    1140

AAATCATTTA TATCTGTACA TTAAAGCAGA TTCCCTCAAT TAGGCAAATT TGGTTAGCCA    1200
```

-continued

```
AGCCCAAGTT ATTGTTTGTA CTTGAAAGTA ATAAAGCTGC ATTTCCTTAA AAATATATTC    1260

TGTAGTTAAG ACTTTGTCTT GCTTTCCGGA ATTCCTGTTT TTCTTTTCCT CTAGAGACCT    1320

CGGCTTGCAA CTGGATCAAA CGCTGTCGAA AGGATGTAAA TAGGCAGAGC AACTGTTACC    1380

AAGAAGGCCA CCACCCCCAC CCAAAGGCAG TGAGGAGTGT GGGGCTTCGT CTGGGCTCCC    1440

CCGAGTCTCA ACAGTAATCA ACAGTCAGGT GTTGATTGCA ACTTTTCAAG GTCAGCCACC    1500

GGGAGTAGCC TATTCCCTCT AGGAACCTTG GAGGGCATAC CTTGCTGGGA CTCAACTTGG    1560

CTGAGAAATG CACAAGATGC CAAAGGAGGA AGGATTATAG GGGCGTGTG TGTGACCCCC     1620

AAGACCGATC TTCCGCTATC ACCCTAATCT CCGGTTCCCC GCTACCCGGG CGGGGTGAG     1680

TATGTGACAT GTGCCTAACT CTCAGCAGCA ACTTCGGCAG CAGGTGTCGA TCCTAACTAA    1740

GCAGGAGCTG CGGCTGCCGG GTGTGCCCTC ACCAAGCCAT GCGAGCCCCG GGCGCGCTTC    1800

TCGCCCGCAT GTCGCGGCTA CTGCTTCTGC TACTGCTCAA GGTGTCTGCC TCTTCTGCCC    1860

TCGGGTCGC CCCTGCGTCC AGAAACGAAA CTTGTCTGGG GGAGAGCTGT GCACCTACAG     1920

TGATCCAGCG CCGCGGCAGG GACGCCTGGG GACCGGGAAA TTCTGCAAGA GACGTTCTGC    1980

GAGCCCGAGC ACCCAGGGAG GAGCAGGGGG CAGCGTTTCT TGCGGGACCC TCCTGGGACC    2040

TGCCGGCGGC CCCGGACCGT GACCCGGCTG CAGGCAGAGG GGCGGAGGCG TCGACAGCCG    2100

GACCCCCGGG ACCTCCAACC AGGCCACCTG TCCCCTGGAG GTGGAAAGGT GCTCGGGGTC    2160

AGGAGCCTTC TGAAACTTTG GGGAGAGGGA ACCCCACGGC CCTCCAGCTC TTCCTTCAGA    2220

TCTCAGAGGA GGAAGAGAAG GGTCCCAGAG GCGCTGTCAT TTCCGGGCGT AGCCAGGAGC    2280

AGAGTGTGAA GACAGTCCCC GGAGCCAGCG ATCTTTTTTA CTGTCCAAGG AGAGCCGGGA    2340

AACTCCAGGG TTCCCACCAC AAGCCCCCAC CCAAGACGGC CAATGGACTG GCGGGGCACG    2400

AAGGGTGGAC AATTGCACTC CCGGGCCGGG CGCTGGCCCA GAATGGATCC TTGGGTGAAG    2460

GAATCCATGA TCCTGGGGGT CCCCGCCGGG GAAACAGCAC GAACCGGCGT GTGAGACTGA    2520

AGAACCCCTT CTACCCGCTG ACCCAGGAGT CCTATGGAGC CTACGCGGTC ATGTGTCTGT    2580

CCGTGGTGAT CTTCGGGACC GGCATCATTG GCAACCTGGC GGTGATGTGC ATCGTGTGCC    2640

ACAACTACTA CATGCGGAGC ATCTCCAACT CCCTCTTGGC CAACCTGGTC TTCTGGGACT    2700

TTCTCATCAT CTTCTTCTGC CTTCCGCTGG TCATCTTCCA CGAGCTGACC AAGAAGTGGC    2760

TGGTGGAGGA CTTCTCCTGC AAGATCGTGC CCTATATAGA GGTCGCTTCT CTGGGAGTCA    2820

CCACTTTCAC CTTATGTGCT CTGTGCATAG ACCGCTTCCG TGCTGCCACC AACGTACAGA    2880

TGTACTACGA AATGATCGAA AACTGTTCCT CAACAACTGC CAAACTTGCT GTTATATGGG    2940

TGGGAGCTCT ATTGTTAGCA CTTCCAGAAG TTGTTCTCCG CCAGCTGAGC AAGGAGGATT    3000

TGGGGTTTAG TGGCCGAGCT CCGGCAGAAA GGTGCATTAT TAAGATCTCT CCTGATTTAC    3060

CAGACACCAT CTATGTTCTA GCCCTCACCT ACGACAGTGC GAGACTGTGG TGGTATTTTG    3120

GCTGTTACTT TTGTTTGCCC ACGCTTTTCA CCATCACCTG CTCTCTAGTG ACTGCGAGGA    3180

AAATCCGCAA AGCAGAGAAA GCCTGTACCC GAGGGAATAA ACGGCAGATT CAACTAGAGA    3240

GTCAGATGAA CTGTACAGTA GTGGCACTGA CCATTTTATA TGGATTGGGC ATTATTCCTG    3300

AAAATATCTG CAACATTGTT ACTGCCTACA TGGCTACAGG GGTTTCACAG CAGACAATGG    3360

ACCTCCTTAA TATCATCAGC CAGTTCCTTT TGTTCTTTAA GTCCTGTGTC ACCCCAGTCC    3420

TCCTTTTCTG TCTCTGCAAA CCCTTCAGTC GGGCCTTCAT GGAGTGCTGC TGCTGTTGCT    3480

GTGAGGAATG CATTCAGAAG TCTTCAACGG TGACCAGTGA TGACAATGAC AACGAGTACA    3540

CCACGGAACT CGAACTCTCG CCTTTCAGTG CCATACGCCG TGAAATGTCC ACTTTTGCTT    3600
```

```
CTGTCGGAAC TCATTGCTGA AGGACAGTAC TTGGTTGGGT CAGATTTATT TGTTTGATTT    3660

TCATATCCCG TGAAAGTTTT TAATTCATAT TTTTCCTTAT AGGGAAAAAT GCAAAAAAGA    3720

AACAATAAAG AAAGAAATAT TAACTACTGT AGAACTGATT TTACAAATTA ATATTTGTGC    3780

TTTGAAAAAA AGTTTCTATT TAGTTATTTA AGAAGAATGA GAAGGCCAAT AGTTTTAGAT    3840

TATTTTATCT GGTATGGTGC TAATATTTTA TTTGAAAAAA GTTACTGCAA CTTAACTTAA    3900

AATTGCTAAC GTTTTTTCTT CTTTTAAAAA TACAATTATT GTATATTAAT TATAGCAATG    3960

TGATTTTGTA GGTTATTTTA TATTTGAGTT GTGATTGAAA GTATGTTGTA TATGGTATTG    4020

TGAGATGATT TGTACTTGGA AGCATTCACA AAGTAGCACC AAATAAATTA CACTTTATTC    4080

TTTAATGTCA TTGTCAATCT ACTTTTAACC AATATTCAAT AAATCTTCTA ATTGCCTTAA    4140

AAAAAAAAAA AAAAA                                                      4156

(2) INFORMATION FOR SEQ ID NO:2:

(i) SEQUENCE CHARACTERISTICS:
        (A) LENGTH: 613 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:2:

Met Arg Ala Pro Gly Ala Leu Leu Ala Arg Met Ser Arg Leu Leu
    -25              -20                 -15

Leu Leu Leu Leu Leu Lys Val Ser Ala Ser Ala Leu Gly Val
    -10                  -5                   1

Ala Pro Ala Ser Arg Asn Glu Thr Cys Leu Gly Glu Ser Cys Ala
  5                  10                  15

Pro Thr Val Ile Gln Arg Gly Arg Asp Ala Trp Gly Pro Gly
 20                  25                  30

Asn Ser Ala Arg Asp Val Leu Arg Ala Arg Ala Pro Arg Glu Glu
 35                  40                  45

Gln Gly Ala Ala Phe Leu Ala Gly Pro Ser Trp Asp Leu Pro Ala
 50                  55                  60

Ala Pro Asp Arg Asp Pro Ala Ala Gly Arg Gly Ala Glu Ala Ser
 65                  70                  75

Thr Ala Gly Pro Pro Gly Pro Pro Thr Arg Pro Val Pro Trp
 80                  85                  90

Arg Trp Lys Gly Ala Arg Gly Gln Glu Pro Ser Glu Thr Leu Gly
 95                 100                 105

Arg Gly Asn Pro Thr Ala Leu Gln Leu Phe Leu Gln Ile Ser Glu
110                 115                 120

Glu Glu Glu Lys Gly Pro Arg Gly Ala Val Ile Ser Gly Arg Ser
125                 130                 135

Gln Glu Gln Ser Val Lys Thr Val Pro Gly Ala Ser Asp Leu Phe
140                 145                 150

Tyr Cys Pro Arg Arg Ala Gly Lys Leu Gln Gly Ser His His Lys
155                 160                 165

Pro Leu Ser Lys Thr Ala Asn Gly Leu Ala Gly His Glu Gly Trp
170                 175                 180

Thr Ile Ala Leu Pro Gly Arg Ala Leu Ala Gln Asn Gly Ser Leu
185                 190                 195
```

-continued

```
Gly Glu Gly Ile His Asp Pro Gly Pro Arg Arg Gly Asn Ser
200                 205                 210

Thr Asn Arg Arg Val Arg Leu Lys Asn Pro Phe Tyr Pro Leu Thr
215                 220                 225

Gln Glu Ser Tyr Gly Ala Tyr Ala Val Met Cys Leu Ser Val Val
230                 235                 240

Ile Phe Gly Thr Gly Ile Ile Gly Asn Leu Ala Val Met Cys Ile
245                 250                 255

Val Cys His Asn Tyr Tyr Met Arg Ser Ile Ser Asn Ser Leu Leu
260                 265                 270

Ala Asn Leu Val Phe Trp Asn Phe Leu Ile Ile Phe Phe Cys Leu
275                 280                 285

Pro Leu Val Ile Phe His Gly Leu Thr Lys Lys Trp Leu Val Glu
290                 295                 300

Asp Phe Ser Cys Lys Ile Val Pro Tyr Ile Glu Val Ala Ser Leu
305                 310                 315

Gly Val Thr Thr Phe Thr Leu Cys Ala Leu Cys Ile Asp Arg Phe
320                 325                 330

Arg Ala Ala Thr Asn Val Gln Met Tyr Tyr Glu Met Ile Glu Asn
335                 340                 345

Cys Ser Ser Thr Thr Ala Lys Leu Ala Val Ile Trp Val Gly Ala
350                 355                 360

Leu Leu Leu Ala Leu Pro Glu Val Val Leu Arg Gln Leu Ser Lys
365                 370                 375

Glu Asp Leu Gly Phe Ser Gly Arg Ala Pro Ala Glu Arg Cys Ile
380                 385                 390

Ile Lys Ile Ser Pro Asp Leu Pro Asp Thr Ile Tyr Val Leu Ala
395                 400                 405

Leu Thr Tyr Asp Ser Ala Arg Lys Trp Trp Tyr Phe Gly Cys Tyr
410                 415                 420

Phe Cys Leu Pro Thr Leu Phe Thr Ile Thr Cys Ser Leu Val Thr
425                 430                 435

Ala Arg Lys Ile Arg Lys Ala Glu Lys Ala Cys Thr Arg Gly Asn
440                 445                 450

Lys Arg Gln Ile Gln Leu Glu Ser Gln Met Asn Cys Thr Val Val
455                 460                 465

Ala Leu Thr Ile Leu Tyr Gly Leu Gly Ile Ile Pro Glu Asn Ile
470                 475                 480

Cys Asn Ile Val Thr Ala Tyr Met Ala Thr Gly Val Ser Gln Gln
485                 490                 495

Thr Met Asp Leu Leu Asn Ile Ile Ser Gln Phe Leu Leu Phe Phe
500                 505                 510

Lys Ser Cys Val Thr Pro Val Leu Leu Phe Cys Leu Cys Lys Pro
515                 520                 525

Phe Ser Arg Ala Phe Met Glu Cys Cys Cys Cys Cys Glu Glu
530                 535                 540

Cys Ile Gln Lys Ser Ser Thr Val Thr Ser Asp Asp Asn Asp Asn
545                 550                 555

Glu Tyr Thr Thr Glu Leu Glu Leu Ser Pro Phe Ser Ala Ile Arg
560                 565                 570

Arg Glu Met Ser Thr Phe Ala Ser Val Gly Thr His Cys
575                 580                 585
```

(2) INFORMATION FOR SEQ ID NO:3:

(i) SEQUENCE CHARACTERISTICS:
        (A) LENGTH: 29 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:3:

```
CACTAAGCTT AATGCGAGCC CCGGGCGCG                                29
```

(2) INFORMATION FOR SEQ ID NO:4:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:4:

```
GAACTTCTAG ACCGTCAGCA ATGAGTACCG AC                            32
```

(2) INFORMATION FOR SEQ ID NO:5:

(i) SEQUENCE CHARACTERISTICS:
        (A) LENGTH: 34 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:5:

```
GTCCAAGCTT GCCACCATGC GAGCCCCGGG CGCG                          34
```

(2) INFORMATION FOR SEQ ID NO:6:

(i) SEQUENCE CHARACTERISTICS:
        (A) LENGTH: 61 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:6:

```
CTAGCTCGAG TCAAGCGTAG TCTGGGACGT CGTATGGGTA GCAGCAATGA GTTCCGACAG   60

A                                                                  61
```

(2) INFORMATION FOR SEQ ID NO:7:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:7:

```
CGGGATCCGC CACCATGCGA GCCCCGGGCG CG                            32
```

(2) INFORMATION FOR SEQ ID NO:8:

```
    (i) SEQUENCE CHARACTERISTICS:
        (A) LENGTH:  29 BASE PAIRS
        (B) TYPE:  NUCLEIC ACID
        (C) STRANDEDNESS:  SINGLE
        (D) TOPOLOGY:  LINEAR (ii) MOLECULE TYPE: Oligonucleotide (xi) SEQUENCE DESCRIPTION:  SEQ ID NO:8:

CGGGATCCCG CTCAGCAATG AGTTCCGAC                                          29
```